United States Patent
Bednarz et al.

(10) Patent No.: US 10,968,192 B2
(45) Date of Patent: Apr. 6, 2021

(54) CRYSTALLINE SOLID FORMS OF N-(1-((2-(DIMETHYLAMINO)ETHYL) AMINO)-2-METHYL-1-OXOPROPAN-2-YL)-4-(4-(2-METHYL-5-((2S,3R,4R,5S,6R)-3,4,5-TRIHYDROXY-6-(METHYLTHIO) TETRAHYDRO-2H-PYRAN-2-YL)BENZYL) PHENYL)BUTANAMIDE AND METHODS OF THEIR SYNTHESIS

(71) Applicant: Lexicon Pharmaceuticals, Inc., The Woodlands, TX (US)

(72) Inventors: Mark Stephen Bednarz, Lower Makefield Township, PA (US); Kuangchu Dai, Shanghai (CN); Jeffrey Manning Eckert, Hazlet, NJ (US); Ngiap-Kie Lim, Dublin, CA (US); Lauren Sirois, San Francisco, CA (US); Wenxue Wu, Princeton Junction, NJ (US); Matthew Mangzhu Zhao, Edison, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 16/579,106

(22) Filed: Sep. 23, 2019

(65) Prior Publication Data
US 2020/0255394 A1   Aug. 13, 2020

Related U.S. Application Data

(60) Provisional application No. 62/736,871, filed on Sep. 26, 2018.

(51) Int. Cl.
*C07D 309/10* (2006.01)
*C07D 207/16* (2006.01)

(52) U.S. Cl.
CPC ......... *C07D 309/10* (2013.01); *C07D 207/16* (2013.01); *C07B 2200/13* (2013.01)

(58) Field of Classification Search
CPC ........................... C07D 309/10; C07D 207/16
See application file for complete search history.

(56) References Cited

U.S. PATENT DOCUMENTS

| 9,200,025 B2 * | 12/2015 | Carson | A61P 3/06 |
| 9,688,710 B2 | 6/2017 | Carson | |
| 10,106,569 B2 | 10/2018 | Carson | |
| 2014/0309178 A1 | 10/2014 | Carson | |
| 2016/0326205 A1 | 11/2016 | Carson | |
| 2018/0244708 A1 | 8/2018 | Carson | |

OTHER PUBLICATIONS

Lauren E. Sirois et al., Org. Process Res, Dev., Dec. 24, 2018, 23(1):45-61.
Mino R Caira ed., Topics in Current Chem., Jan. 1, 1999, 198:163-208.
International Search Report for PCT Application No. PCT/US2019/052414 to Lexicon Pharmaceuticals, Inc., dated Jan. 13, 2020.

* cited by examiner

*Primary Examiner* — Rebecca L Anderson
(74) *Attorney, Agent, or Firm* — Max Bachrach

(57) ABSTRACT

Methods of preparing, and solid forms of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide, and salts, solvates and cocrystals thereof, are disclosed.

5 Claims, 2 Drawing Sheets

Figure 1:
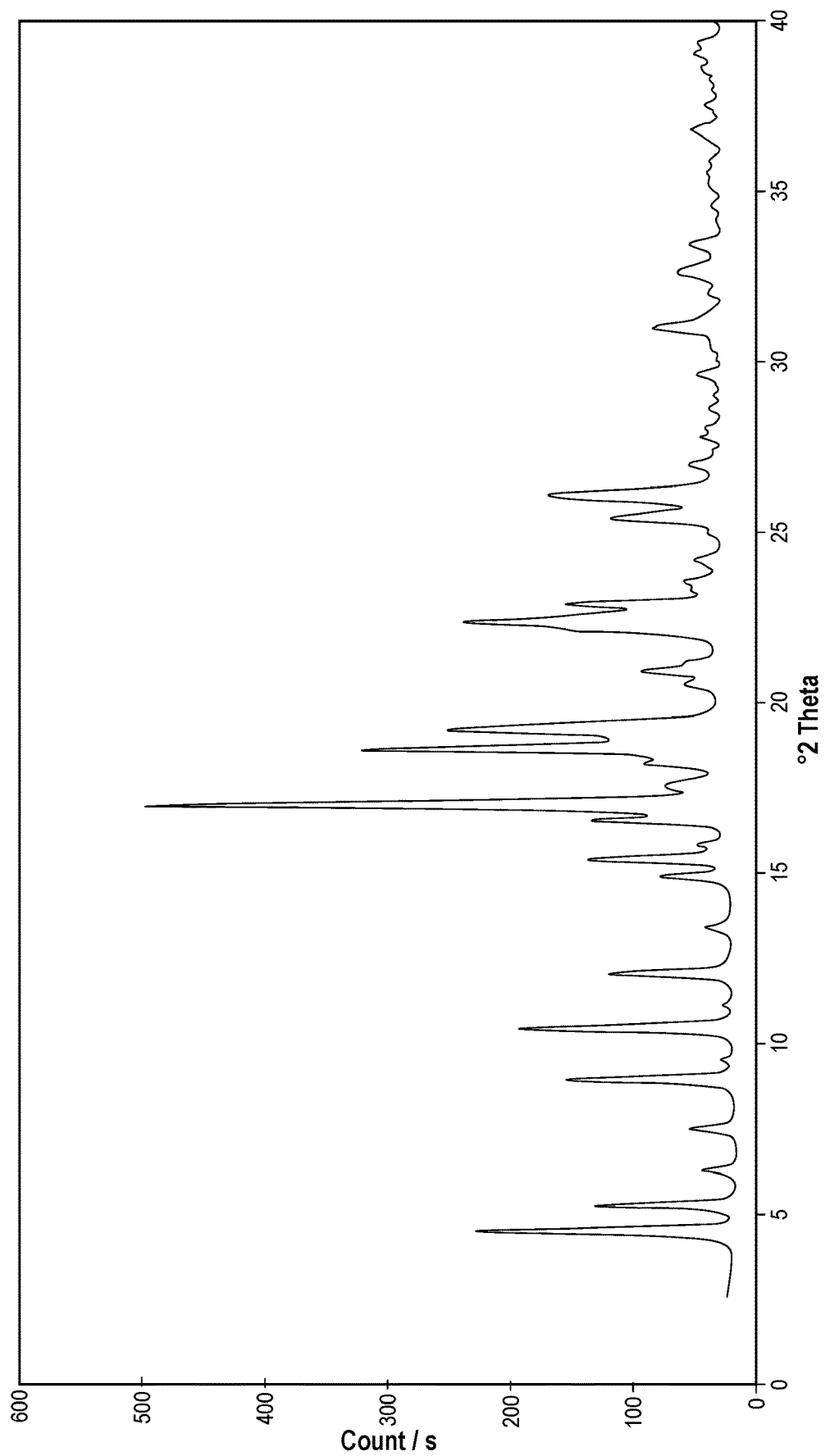

CRYSTALLINE SOLID FORMS OF N-(1-((2-(DIMETHYLAMINO)ETHYL)AMINO)-2-METHYL-1-OXOPROPAN-2-YL)-4-(4-(2-METHYL-5-((2S,3R,4R,5S,6R)-3,4,5-TRIHYDROXY-6-(METHYLTHIO)TETRAHYDRO-2H-PYRAN-2-YL)BENZYL)PHENYL)BUTANAMIDE AND METHODS OF THEIR SYNTHESIS

1. FIELD OF THE INVENTION

This disclosure relates to crystalline solid forms of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide.

2. BACKGROUND OF THE INVENTION

Type 2 diabetes mellitus is a chronic disease characterized by hyperglycemia caused by hepatic glucose production, a deficiency in insulin secretion, and/or peripheral insulin resistance. In recent years, inhibition of the sodium glucose co-transporter (SLGT), of which there are two types (SGLT1 and SGLT2), has emerged as an attractive method of treating diabetes. And while SGLT inhibitors currently on the market (e.g., canagliflozin, dapagliflozin, and empagliflozin) target SGLT2, drugs that target SGLT1 hold considerable promise. For example, sotagliflozin, which targets both SGLT1 and 2, has been shown to have potential efficacy in the treatment of Type 1 diabetes. See, e.g., Garg, S. K., et al., "Effects of Sotagliflozin Added to Insulin in Patients with Type 1 Diabetes," *New England J. Med.*, Sep. 13, 2017.

Other SGLT1 inhibitors that exhibit dose-dependent reductions in HbA1c when administered to mice are disclosed in U.S. Pat. No. 9,200,025. But while such testing can help identify a lead drug development candidate, significant additional research is necessary to take a compound prepared on bench scale to one that can be manufactured on a large sale with the consistency, purity, and physical characteristics that allow for commercial drug formulation.

Different solid forms of the same compound can have substantially different properties. For example, the amorphous form of a drug may exhibit different dissolution and bioavailability characteristics than its crystalline form, polymorphs of a crystalline form may also differ in their solubilities, thermal stabilities, and other characteristics, and different salts and co-crystals of a compound may be easier to manufacture with greater purity than others. Different solid forms of a drug may have different handling properties (e.g., flowability, compressibility), dissolution rates, solubilities and stabilities, all of which can affect the manufacture of dosage forms.

Compounds may exist in one or more salts, crystalline forms, or co-crystals, but their existence and characteristics cannot be predicted with any certainty. Different forms may have different physical properties such as, for example, melting temperatures, heats of fusion, solubilities, dissolution rates, and/or vibrational spectra as a result of the arrangement or conformation of the molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph), mechanical changes (e.g., tablets crumble on storage as a kinetically favored polymorph converts to thermodynamically more stable polymorph), or both (e.g., tablets of one polymorph are more susceptible to breakdown at high humidity). In addition, the physical properties of a crystalline form may be important in processing; for example, one polymorph might be more likely to form solvates or might be difficult to filter and wash free of impurities (e.g., particle shape and size distribution might be different between polymorphs). Polymorphs may be characterized by a variety of methods known in the art, including X-ray powder diffraction, and melting point.

No standard procedure exists for the preparation of all possible solid forms of a compound, and the chemical and physical properties of a form (e.g., stability, flowability) that affect its use as a pharmaceutical cannot be predicted with any certainty. Yet these characteristics play a critical role in pharmaceutical formulation. For example, capsules of the anti-retroviral drug ritonavir were withdrawn from the market in the late 1990s after it was discovered that the manufactured polymorphic form of the drug converted to a more thermodynamically stable, but less therapeutically effective form, within the capsules. See, e.g., S. L. Morisette et al., *Proc. Natl. Acad. Sci. USA*. 100 (5): 2180-84. For reasons such as this, regulatory authorities (e.g., the U.S. Food and Drug Administration) may require the identification of solid (e.g., polymorphic) forms of a new drug substance before approving products containing it. A. Goho, *Science News* 166(8):122-123 (2004).

3. SUMMARY OF THE INVENTION

This disclosure is directed to solid forms of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide:

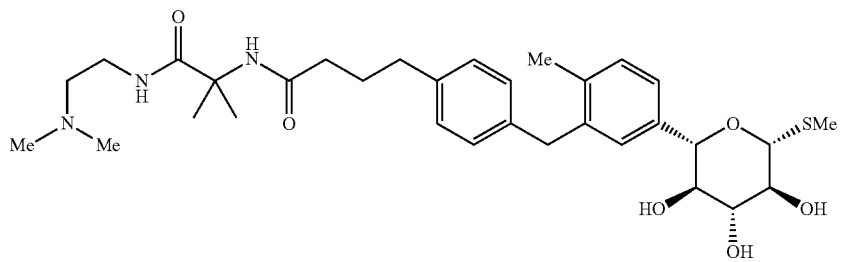 [SMILES: CS[C@H]1O[C@@H](c2ccc(C)c(Cc3ccc(CCCC(=O)NC(C)(C)C(=O)NCCN(C)C)cc3)c2)[C@H](O)[C@@H](O)[C@@H]1O]

and pharmaceutically acceptable salts, solvates, and co-crystals thereof.

Particular solid forms include amino acid co-crystals of N-(1-((2-(dimethylamino)ethyl)-amino)-2-methyl-1-oxo-propan-2-yl)-4-(4-(2-methyl-5-((2S,3R,4R,5S,6R)-3,4,5-tri-hydroxy-6-(methylthio)tetrahydro-2H-pyran-2-yl)benzyl) phenyl)butanamide. A particular amino acid is L-proline.

This disclosure is also directed to pharmaceutical compositions comprising the solid forms described herein.

This disclosure is also directed to processes for the manufacture of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide and pharmaceutically acceptable salts, solvates, and co-crystals thereof.

This disclosure is also directed to methods of treating, managing, and preventing various diseases and conditions, which comprise the use of the solid forms described herein. Particular methods include the use of a solid form of N-(1-((2-(dimethylamino)ethyl)-amino)-2-methyl-1-oxo-propan-2-yl)-4-(4-(2-methyl-5-((2S,3R,4R,5S,6R)-3,4,5-tri-hydroxy-6-(methylthio)tetrahydro-2H-pyran-2-yl)benzyl) phenyl)butanamide for treating, preventing, or managing a metabolic disease or disorder. Others include the use of a solid form of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide for the manufacture of a medicament for use in treating, preventing or managing a metabolic disease or disorder.

4. BRIEF DESCRIPTION OF THE FIGURES

FIG. 1 is an X-ray powder diffraction (XRPD) pattern of what is referred to herein as Form II of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline. The diffractogram was obtained at room temperature using a Bruker D8 system using copper K$\alpha$ radiation (40 kV/40 mA), a range of 2-50 degrees 2$\theta$, a step time of 37 s, and a LynxEye detector with a 3 degree window.

Figure 2:
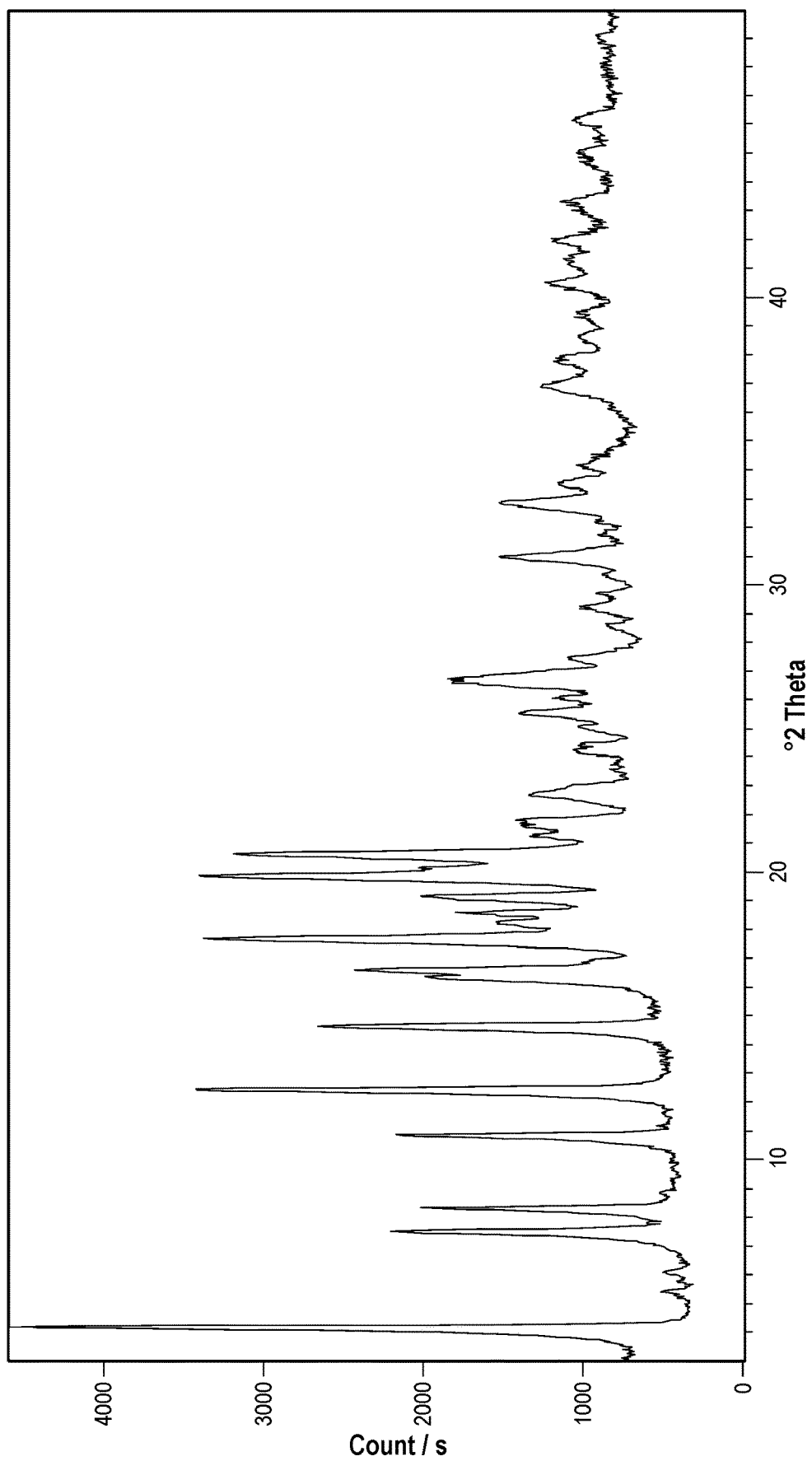

FIG. 2 is an XRPD pattern of what is referred to herein as Form III of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline. The diffractogram was obtained at room temperature using a Bruker D8 system using copper K$\alpha$ radiation (40 kV/40 mA), a range of 2-50 degrees 2$\theta$, a step time of 37 s, and a LynxEye detector with a 3 degree window.

5. DETAILED DESCRIPTION OF THE INVENTION

This disclosure is directed, in part, to solid (e.g., crystalline) forms of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide, and pharmaceutically acceptable salts, solvates, and co-crystals thereof. The compound is a potent inhibitor of sodium glucose co-transporter type 1 (SGLT1), and may be useful in the treatment of diabetes and other metabolic disorders. See, e.g., U.S. Pat. No. 9,200,025, Examples 6.39, 6.40.

5.1. Definitions

Unless otherwise indicated, the term "alkyl" means a straight chain or branched hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, 2,2,4-trimethylpentyl, nonyl, decyl, undecyl and dodecyl.

Unless otherwise indicated, the term "aryl" means an aromatic ring or an aromatic or partially aromatic ring system composed of carbon and hydrogen atoms. An aryl moiety may comprise multiple rings bound or fused together. Particular aryl moieties comprise from six to twelve carbon atoms in their rings, and are referred to as $C_{6-12}$ aryl. Examples of aryl moieties include anthracenyl, azulenyl, biphenyl, fluorenyl, indanyl, indenyl, naphthyl, phenanthrenyl, phenyl, 1,2,3,4-tetrahydro-naphthalenyl, and tolyl.

Unless otherwise indicated, the terms "halogen" and "halo" encompass fluorine, chlorine, bromine, and iodine.

Unless otherwise indicated, the term "palladium pre-catalyst" refers to a palladium compound which forms a palladium catalyst when combined with suitable ligands.

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more stereogenic centers, but which do not indicate stereochemistry (e.g., with bolded or dashed lines), encompasses pure stereoisomers and mixtures (e.g., racemic mixtures) thereof. Similarly, names of compounds having one or more stereogenic centers that do not specify the stereochemistry of those centers encompass pure stereoisomers and mixtures thereof.

"Solvate" refers to a compound provided herein, or a salt or co-crystal thereof, that further includes a stoichiometric or non-stoichiometric amount of solvent bound by non-covalent intermolecular forces. Where the solvent is water, the solvate is a hydrate.

The term "amorphous" or "amorphous form" is intended to mean that the substance, component, or product in question is not substantially crystalline as determined, for instance, by XRPD or where the substance, component, or product in question, for example is not birefringent when viewed microscopically. In certain embodiments, a sample comprising an amorphous form of a substance may be substantially free of other amorphous forms and/or crystalline forms.

The term "anti-solvent" refers to a liquid that is added to a solvent to reduce the solubility of a compound in that solvent, in some instances, resulting in precipitation of the compound.

The term "crystalline form" of a compound can refer to any crystalline form of the compound as a free acid, the compound as a free base, as an acid addition salt of the compound, a base addition salt of the compound, a complex of the compound, a solvate (including hydrate) of the compound, a clathrate of the compound, or a co-crystal of the compound. The term "solid form" of a compound can refer to any crystalline form of the compound or any amorphous form of the compound as a free acid, the compound as a free base, as an acid addition salt of the compound, an base addition salt of the compound, a complex of the compound, a clathrate of the compound, a co-crystal, or a solvate (including hydrate) of the compound, or a co-precipitate of the compound. In many instances, the terms "crystalline form" and "solid form" can refer to those that are pharmaceutically acceptable, including, for example, those of pharmaceutically acceptable addition salts, pharmaceutically acceptable complexes, pharmaceutically acceptable solvates, a clathrate of the compound, pharmaceutically acceptable co-crystals, and pharmaceutically acceptable co-precipitates.

Unless otherwise indicated, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Unless otherwise indicated, the term "locally acting" refers to compounds that have poor systemic exposure but still produce a desired pharmacodynamic effect. Particular locally acting compounds have a maximum plasma concentration (Cmax) of less than 20 or 10 nM when orally administered at a dose of 10 mg/kg to a mouse, rat or human. Systemic exposure (e.g., Cmax) can be measured by methods well known in the art, including liquid chromatography mass spectrometry.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgus monkey, a chimpanzee and a human), and for example, a human.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

5.2. Forms of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide This disclosure is directed to solid forms of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide:

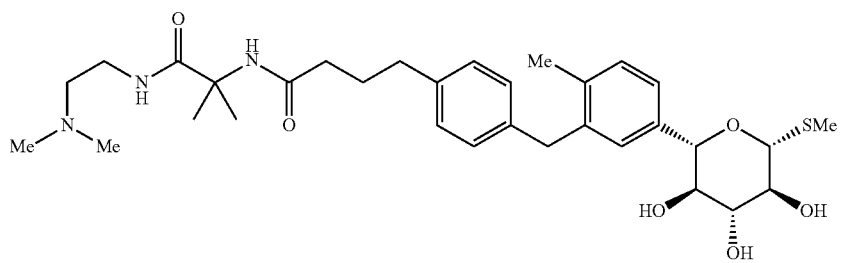 [SMILES: CS[C@H]1O[C@@H](c2ccc(C)c(Cc3ccc(CCCC(=O)NC(C)(C)C(=O)NCCN(C)C)cc3)c2)[C@H](O)[C@@H](O)[C@@H]1O]

and pharmaceutically acceptable salts, solvates, and co-crystals thereof. Particular salts of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide include naphthalene-1,5-disulfonate, phosphate, L-tartrate and hydrochloride salts. Particular co-crystals are co-crystals of amino acids.

Prior to this invention, there were no known crystalline forms of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide: extensive screens using a wide range of potential salts, co-crystals and reaction conditions yielded sticky tar or amorphous material.

Significant further research directed at discovering useful and stable solid forms of the compound finally led to the discovery of a few crystalline forms of the free base, solvates, and co-crystals. Of particular interest was an L-proline co-crystal of N-(1-((2-(dimethylamino)ethyl)-amino)-2-methyl-1-oxopropan-2-yl)-4-(4-(2-methyl-5-((2S, 3R,4R,5S,6R)-3,4,5-trihydroxy-6-(methylthio)tetrahydro-2H-pyran-2-yl)benzyl)phenyl)butanamide. Although polymorphism studies led to the identification of eleven different Raman spectroscopic classes of the co-crystal, three were dominated by amorphous material and most were unstable (i.e., lose their crystallinity or convert to other forms) upon drying. Only two forms—referred to herein as Form II and Form III—of the L-proline co-crystal were stable enough to be useful in pharmaceutical formulations.

Thus, one aspect of this invention is directed to crystalline forms of N-(1-((2-(dimethylamino)ethyl)-amino)-2-methyl-1-oxopropan-2-yl)-4-(4-(2-methyl-5-((2S,3R,4R,5S,6R)-3, 4,5-trihydroxy-6-(methylthio)tetrahydro-2H-pyran-2-yl) benzyl)phenyl)butanamide L-proline:

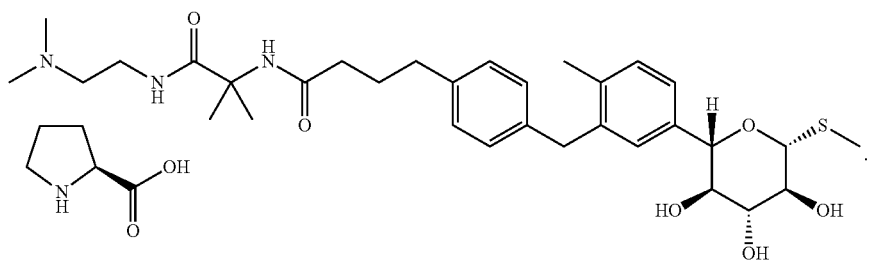

A particular crystalline form of N-(1-((2-(dimethylamino) ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline is Form II, which has a melting point of approximately 147° C. (i.e., 147±5.0° C.) as determined by differential scanning calorimetry (DSC). When referring to melting points, the term "approximately" as used herein means±5.0 degrees Celsius. It should also be noted that when forms are prepared from solvents (e.g., ethanol), melting points are measured after drying unless otherwise indicated.

An example of Form II has an X-ray powder diffraction (XRPD) pattern obtained at room temperature using copper Kα radiation that comprises peaks at one or more of 4.5, 5.3, 10.5, 12.1, 17.1, 18.8, 19.3, 22.3, 26.1, and 26.2±0.5 degrees 2θ. (The recitation of an error value, e.g., ±0.5 degrees 2θ, at the end of a list of several degrees 2θ values is meant to indicate an approximate value of ±0.5 degrees 2θ for each of the listed degrees 2θ values.) A particular diffraction pattern contains peaks at approximately 4.5, 5.3, and/or 10.5 degrees 2θ. Another contains peaks at approximately 10.5, 12.1, and/or 17.1 degrees 2θ. Another contains peaks at approximately 18.8, 19.3, and/or 22.3 degrees 2θ. A particular example of Form II has an XRPD pattern substantially the same as that shown in FIG. 1.

Another crystalline form of N-(1-((2-(dimethylamino) ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline is Form III, which has a melting point of approximately 150° C. (i.e., 150±5.0° C. as determined by DSC.

An example of Form III has an XRPD pattern obtained at room temperature using copper Kα radiation that comprises peaks at one or more of 4.2, 7.5, 8.3, 10.9, 12.5, 14.7, 16.6, 17.7, 19.8, and 20.6±0.5 degrees 2θ. A specific example of Form III has an XRPD pattern that contains peaks at approximately (i.e., ±0.5 degrees 2θ) 4.2, 7.5, 8.3, 10.9, 12.5, 14.7, 16.6, 17.7, and/or 19.9 degrees 2θ when obtained at room temperature using copper Kα radiation. A particular diffraction pattern contains peaks at approximately 4.2, 7.5, and/or 8.3 degrees 2θ. Another contains peaks at approximately 8.3, 10.9, and/or 12.5 degrees 2θ. Another contains peaks at approximately 14.7, 16.6, and/or 17.7 degrees 2θ. A particular example of Form III has an XRPD pattern substantially as described in FIG. 2.

Crystalline forms II and III of N-(1-((2-(dimethylamino) ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline offer significant advantages when compared to amorphous forms of the compound, which can be difficult to obtain with the purity and at the scale necessary for pharmaceutical manufacture. Forms II and III can be obtained on a large scale and with high purity, unlike other forms of the compound. Because of its stability, Form III is particularly preferred for use as an active pharmaceutical ingredient.

This disclosure encompasses solids that are mixtures of both amorphous and crystalline forms. Certain such solids comprise crystalline N-(1-((2-(dimethylamino)ethyl)-amino)-2-methyl-1-oxopropan-2-yl)-4-(4-(2-methyl-5-((2S, 3R,4R,5S,6R)-3,4,5-trihydroxy-6-(methylthio)tetrahydro-2H-pyran-2-yl)benzyl)phenyl)butanamide or a pharmaceutically acceptable salt thereof in an amount of at least approximately 50, 75, 80, 85, 90, 95 or 99 weight percent.

This disclosure also encompasses mixtures of crystalline forms, such as mixtures of forms II and III of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl) butanamide L-proline. In one embodiment of the invention, the compound Form II or Form III is substantially pure. Reference to "substantially pure" with respect to a particular form means the form makes up at least 50% of that compound (e.g., Compound I) present. In other embodiments, a particular form makes up at least 75%, at least 85%, at least 90%, at least 95%, at least 98%, at least 99%, or about 94%-98% of compound (e.g., Compound I) present.

5.3. Methods of Synthesis

This disclosure encompasses processes for preparation of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl) phenyl)butanamide free base, as well as salts, solvates, and co-crystals thereof.

One embodiment of the invention encompasses a process for preparing N-(1-((2-(dimethylamino)ethyl)-amino)-2- methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide:

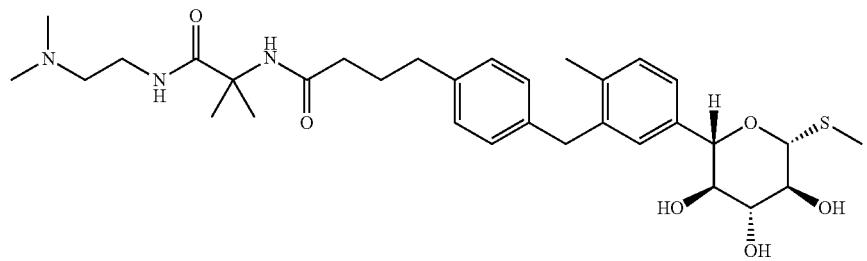

or a pharmaceutically acceptable salt, solvate or co-crystal thereof, which process comprises:

(i) providing a mixture by contacting a compound of formula (II) with a compound of formula (III) in the presence of a palladium catalyst and a base:

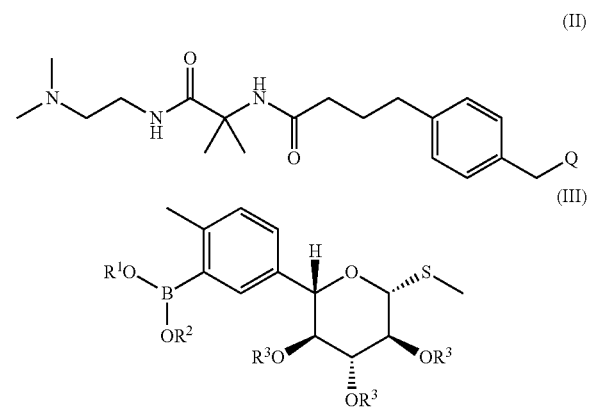

wherein Q is a leaving group; $R^1$ and $R^2$ are $C_{1-5}$ alkyl, or $R^1$ and $R^2$ are joined and together with the atoms to which they are attached from a cyclic boronate; and each $R^3$ is a protecting group;

(ii) isolating from the mixture a compound of formula (IV):

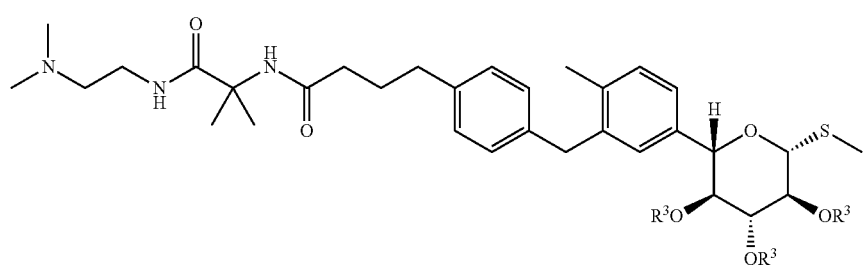

and (iii) deprotecting the compound of formula (IV).

In some embodiments, Q is halide, a triflate, a phosphate, an acetate, a carbonate or a nitrogen leaving group (e.g., an N,N-ditosylbenzylamine). In one embodiment, halide is F, Cl, Br or I. In another, halide is Br or I. In another, halo is Br or Cl. In another, Q is a triflate. In another, Q is —OC(=O)OR or OP(=O)O(R)$_2$, wherein R is $C_{1-5}$ alkyl or aryl. In another, Q is a phosphate such as an alkyl phosphate or an aryl phosphate. In another, Q is an acetate. In another, Q is a carbonate such as an alkyl carbonate or an aryl carbonate. In one embodiment, Q is methylcarbonate.

The protecting group $R^3$ may be any protecting group for protection of hydroxy groups (e.g., protecting groups described in Wuts, P. G. M. and Greene, T. W., *Greene's Protective Groups in Organic Synthesis*, fifth edition). In some embodiments, each $R^3$ is an acetyl, benzyl or benzoyl group. In one embodiment, each $R^3$ is a benzyl group. In another, $R^3$ is a benzoyl group. In another, $R^3$ is a carboxybenzyl group. In another, each $R^3$ is an acetyl group.

The palladium catalyzed reaction of the compound of formula (II) with the compound of formula (III) is a Suzuki coupling reaction, which may be carried out in the presence of any suitable base. In one instance, the base is chosen so that $R^3$ groups are not cleaved under the reaction conditions. In one instance the base is KOAc or $K_2CO_3$. In one example, the base is KOAc. In another, the base is $K_2CO_3$.

The palladium catalyst for the Suzuki coupling of the compound of formula (II) with the compound of formula (III) is formed from a palladium pre-catalyst and diphosphine ligands. In one embodiment, the palladium pre-catalyst is [Pd(allyl)Cl]$_2$ or Pd(OAc)$_2$. In one instance, the palladium pre-catalyst is [Pd(allyl)Cl]$_2$. In another, the palladium pre-catalyst is Pd(OAc)$_2$. In such embodiments, the diphosphine ligand is 1,4-bis(diphenylphosphino)pentane (DPPPentane), 1,4-bis(diphenylphosphino)butane (DPPPButane), 1,1'-bis(diphenylphosphino)ferrocene (DPPF), 4,5-bis(diphenylphosphino)-9,9-dimethylxanthene (xantphos), or bis[(2-diphenylphosphino)phenyl] ether (DPEPhos). In particular embodiments of the invention, the palladium catalyzed reaction of the compound of formula (II) with the compound of formula (III) utilizes $K_2CO_3$ as the base and the palladium catalyst is formed from [Pd(allyl)Cl]$_2$ and 1,4-bis(diphenylphosphino)butane. In other embodiments, the base is KOAc and the palladium catalyst is formed from Pd(OAc)$_2$ and 1,1'-bis(diphenylphosphino)

ferrocene. In some embodiments, the ratio of the pre-catalyst to ligand used to form the palladium catalyst is about 1:1. In some instances, the reaction mixture for the Suzuki coupling comprises about 0.5 mole % of the pre-catalyst and about 1.1 mol % of the ligand, and about 1.1 equivalents of the compound of formula (II) relative to the equivalents of the compound of formula (III). In some instances, the compound of formula (IV) is isolated with a non-aqueous work up.

In some embodiments, for the process described above, $R^1$ and $R^2$ are methyl. In other embodiments, for the process described above, $R^1$ and $R^2$ are joined and together with the atoms to which they are attached from a cyclic boronate. In some of such embodiments, the cyclic boronate is a pinacolboronate. In a specific embodiment, for the process described above, $R^3$ in formula (III) is acetyl.

((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline is obtained in crystal form. In some of such instances, the N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline obtained in crystal form is Form III.

Scheme 1 shows one approach for the preparation of a compound of formula (IV), and conversion of the compound of formula (IV) to Form III of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline.

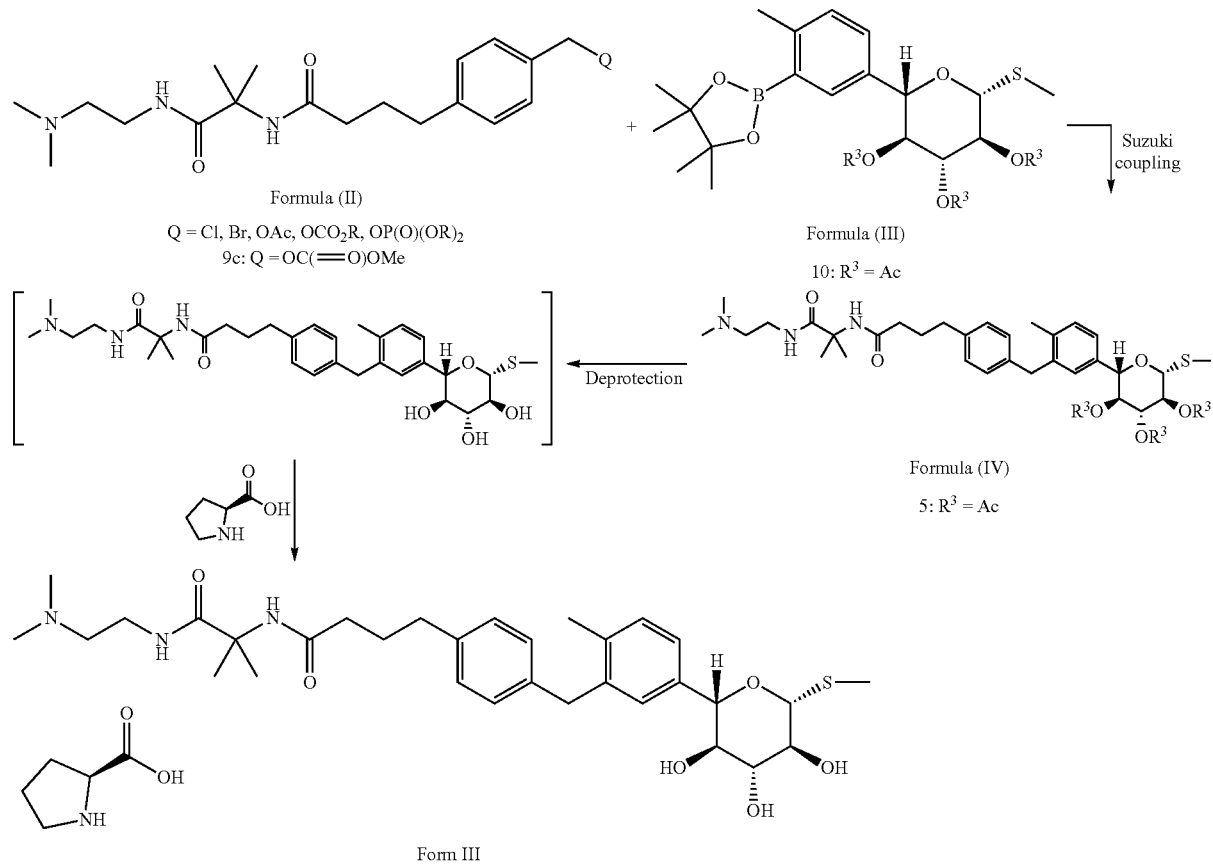

In an embodiment of the process described above, the compound of formula (IV) is deprotected by contacting the compound of formula (IV) with a base and an alcohol (e.g., methanol, ethanol, isopropanol). In one instance, the base is sodium methoxide and the alcohol is ethanol.

In an additional embodiment, the process described above further comprises contacting the deprotected compound of formula (IV) with a solution of L-proline in ethanol and water under conditions sufficient to obtain N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline. In some of such instances, the N-(1-

A Suzuki coupling of the compound of formula (II) with a compound of formula (III) to obtain a compound of formula (IV) is described in Example 6.9. The reaction conditions are chosen to minimize hydrolysis of protecting groups in the compound of formula (IV). By way of example only, in an embodiment, for the Suzuki coupling, weaker bases such $K_2CO_3$ and KOAc are preferred over stronger bases such as $Cs_2CO_3$ or $K_3PO_4$. By way of example only, in one embodiment, solvents that are weaker nucleophiles (e.g., isopropanol) are preferred over solvents that are stronger nucleophiles (such as water, methanol, ethanol or butanol). In one embodiment, a mixture of isopropanol/water is used as a solvent for the Suzuki coupling. By way of example only, the reaction temperature for the Suzuki coupling is from about 50° C. to about 70° C. In an embodiment, weaker bases such K₂CO₃, one or more solvents that comprise weaker nucleophiles (e.g., isopropanol), and moderate reaction temperatures ranging from about 50° C. to about 70° C. are suitable for the Suzuki coupling. It will be understood that coupling conditions may be varied by one of skill in the art and all such variations are contemplated within the scope of embodiments presented herein. Deprotection of the compound of formula IV provides Compound I.

N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline can be prepared by adding L-proline to a solution of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide, stirring, and filtering the resulting precipitate. In a particular embodiment, the solvent comprises methanol, ethanol, or isopropanol. In a particular embodiment, the solution comprising the free base is maintained at a temperature of from approximately 35-50° C., and is subsequently cooled after addition of the L-proline solution.

For any embodiments of the process described above, provided herein is a process for the preparation of the compound of formula (II)

(II)

the process comprising:

(i) contacting a compound of formula 11 with compound 8 under conditions sufficient to obtain a compound of formula 9:

wherein R⁴ is a silyl protecting group or a tetrahyropyranyl group;

(ii) deprotecting the compound of formula 9 to obtain compound 9b

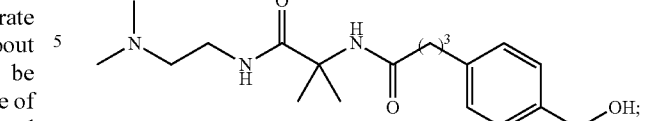

and (iii) contacting compound 9b with Q-Cl or Q-OMe in the presence of a base under conditions sufficient to obtain the compound of formula (II).

In an embodiment of the process for preparation of formula (II) described above, the conditions sufficient to provide the compound of formula 9 may include any conditions suitable for forming amide bonds. In some embodiments, the reaction is carried out in the presence of pivaloyl chloride and trimethylamine in aprotic solvents. In some instances, the reaction is carried out at a temperature ranging from about −25° C. to about 35° C. In such instances, the aprotic solvents include and are not limited to tetrahydrofuran, toluene, acetonitrile, dimethylformamide and combinations thereof. In some instances, the solvent is a mixture of toluene and tetrahydrofuran. In certain instances, the compound of formula 9 is crystallized from a mixture of methyl tert-butyl ether (MTBE) and n-heptane. In certain embodiments, R⁴ is a silyl protecting group. In other embodiments, R⁴ is a tetrahydropyranyl group. In certain instances, deprotection of the compound of formula 9 is carried out in the presence of an acid (e.g., aqueous HCl in methanol, TFA in acetonitrile).

In some embodiments, the conditions sufficient for the reaction of compound 9b with Q-Cl include suitable bases such as, for example, pyridine and further comprise additional sacrificial amines such as, for example, diethylamine or dipropylamine. In some embodiments, Q-Cl is methyl chloroformate.

In other embodiments, the conditions sufficient for the reaction of compound 9b with Q-OMe include suitable transesterification conditions. In some embodiments, the conditions suitable for the reaction of Q-OMe with compound 9b include a base such as, for example, potassium t-butoxide or sodium methoxide. In a specific embodiment, Q-OMe is methyl carbonate (MeO—C(=O)—OMe).

The compound of formula 11 can be prepared by a process comprising in situ activation of zinc, the process comprising:

(i) contacting compound 29 with zinc dust and at least one additive to form compound 28 in situ:

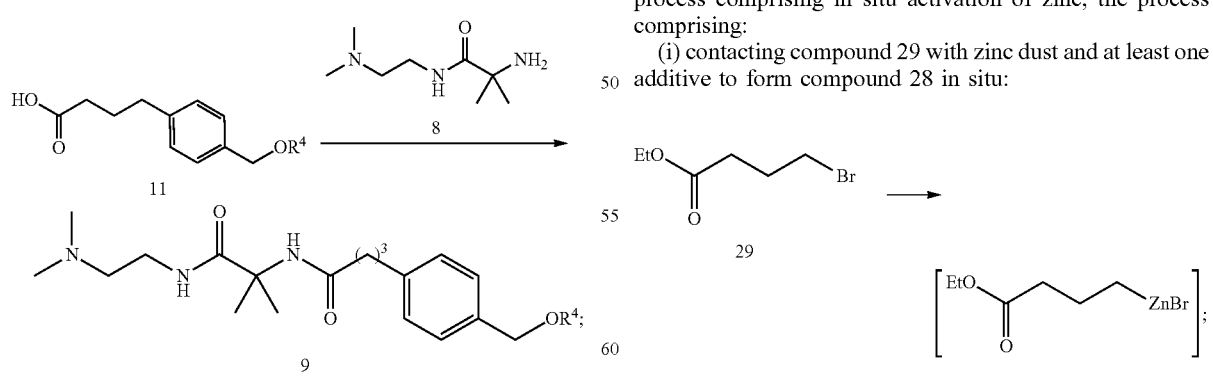

and (ii) contacting compound 28 with a compound of formula 26 in the presence of a palladium catalyst to obtain the compound of formula 27:

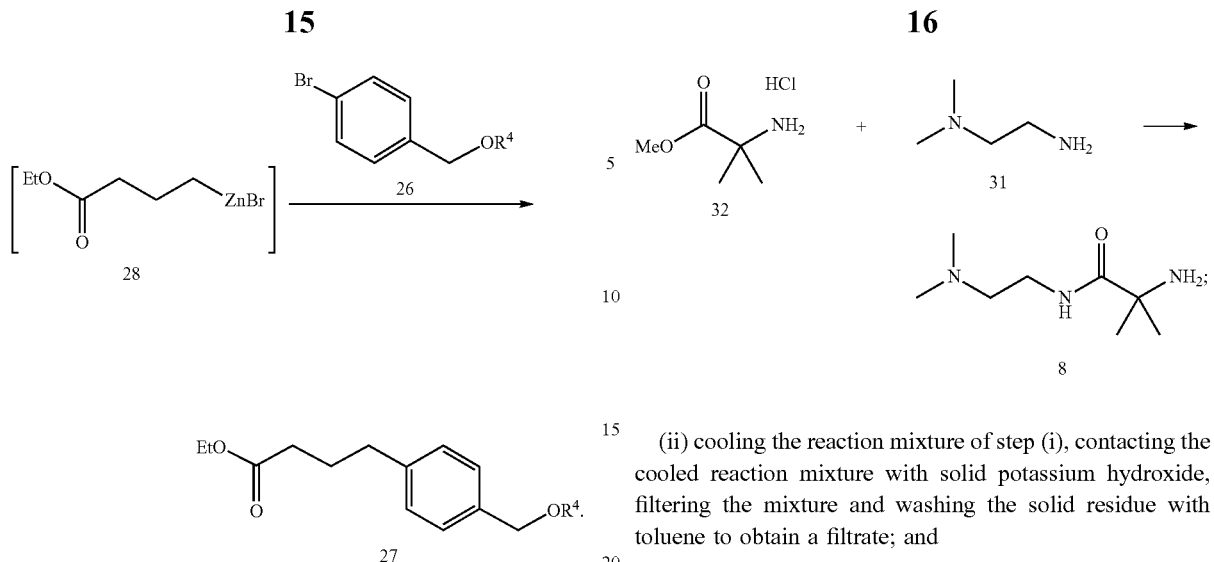

In a particular embodiment of the invention, the process for the synthesis of the compound of formula 11 further comprises hydrolysis of the ester in the compound of formula 27.

In certain embodiments, the at least one additive is TMSCl and LiCl. In some instances, the at least one additive is TMSCl and LiCl; or TMSCl. In some of such instances, $R^4$ is a tetrahydropyranyl group. In some instances, the palladium catalyst is Pd(OAc)$_2$/SPhos, Pd(OAc)$_2$/PPh$_3$, PdCl$_2$(PPh$_3$)$_2$ or PdCl$_2$dppf. In one example, the palladium catalyst is Pd(OAc)$_2$/SPhos. In some of such embodiments, the ratio of SPhos:Pd(OAc)$_2$ ranges from about 2:1 to about 10:1. In some instances, about 0.1 mole % of the palladium catalyst is present in the reaction mixture.

In an embodiment, the reaction of compound 28 with the compound of formula 26 comprises a portionwise addition of compound 28 to a mixture comprising a compound of formula 26. In certain embodiments, the reaction temperature for the formation of the compound of formula 27 is about 35° C. to about 60° C.

Compound 8 is preferably prepared by processes comprising:

(i) reacting compound 31 with compound 32 by heating compound 32 in an excess of compound 31:

(ii) cooling the reaction mixture of step (i), contacting the cooled reaction mixture with solid potassium hydroxide, filtering the mixture and washing the solid residue with toluene to obtain a filtrate; and (iii) removing excess compound 31 from the filtrate of step (ii) by co-distillation with toluene to obtain compound 8.

Compound 8 may alternatively be prepared by contacting compound 30 with compound 31 in the presence of 1,1'-carbonyldiimidazole (CDI) and isolating compound 8-boc:

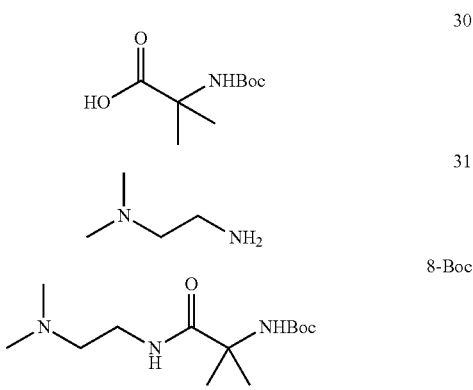

Removal of the Boc protecting group in compound 8-Boc provides compound 8.

Scheme 2 shows one approach for the preparation of a compound of formula (II).

Scheme 2

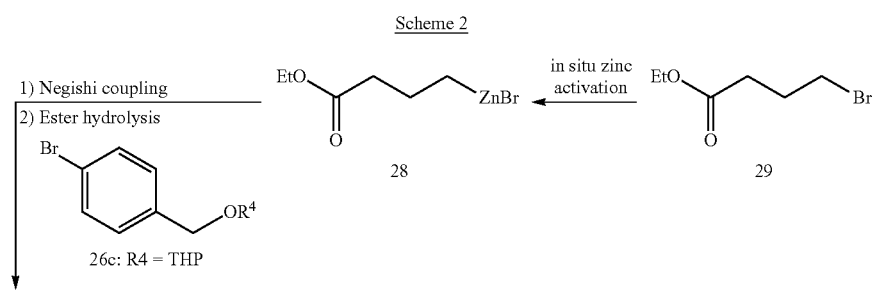

26c: R4 = THP

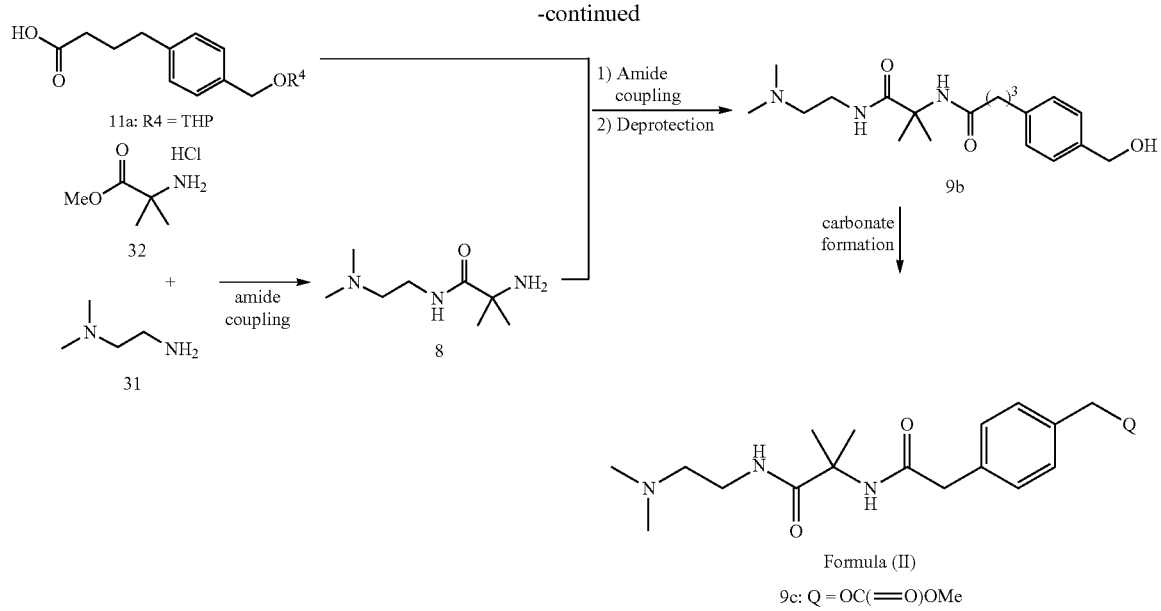

The activation of zinc is carried out in situ and the zinc reagent is used in the Negishi coupling reaction without isolation. For the Negishi coupling, a solution of the alkyl zinc is added in portions to a mixture of the catalyst and aryl bromide, as described in Example 6.6. The amine 8 is prepared as described in Example 6.5 and is preferably isolated without an aqueous work up. Amide coupling of compound 11a with amine 8 is conducted under any suitable amide coupling conditions known to one of skill in the art. In one example, the amide coupling of compound 11a with amine 8 is conducted in the presence of pivalolyl chloride and a base as described in example 6.7. The conversion of compound 9b to a compound of Formula (II) is carried out as described in Example 6.7. In one example, compound 9b is converted to compound 9c in the presence of excess dimethyl carbonate.

A particular compound of formula (III) is (2S,3S,4R,5S,6R)-2-(4-methyl-3-(4,4,5,5-tetramethyl-1,3,2-dioxaborolan-2-yl)phenyl)-6-(methylthio)tetrahydro-2H-pyran-3,4,5-triyl triacetate (compound 10):

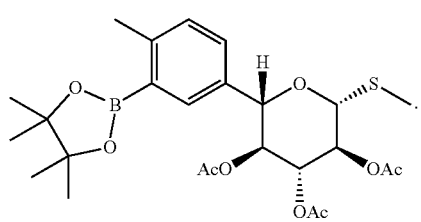

In one embodiment of the invention, compound 10 is prepared by borylating (2S,3S,4R,5S,6R)-2-(3-chloro-4-methyl phenyl)-6-(methylthio)tetrahydro-2H-pyran-3,4,5-triyl triacetate (compound 20):

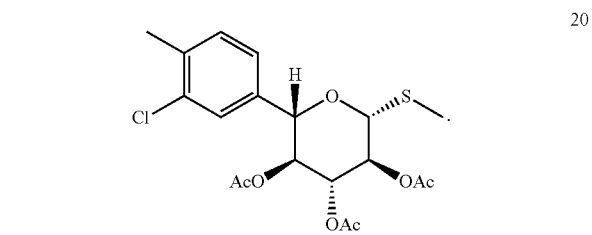 [SMILES: CS[C@H]1O[C@@H](c2ccc(C)c(Cl)c2)[C@H](OC(C)=O)[C@@H](OC(C)=O)[C@@H]1OC(C)=O]

Scheme 3 below shows one approach for the preparation of a compound of formula (III).

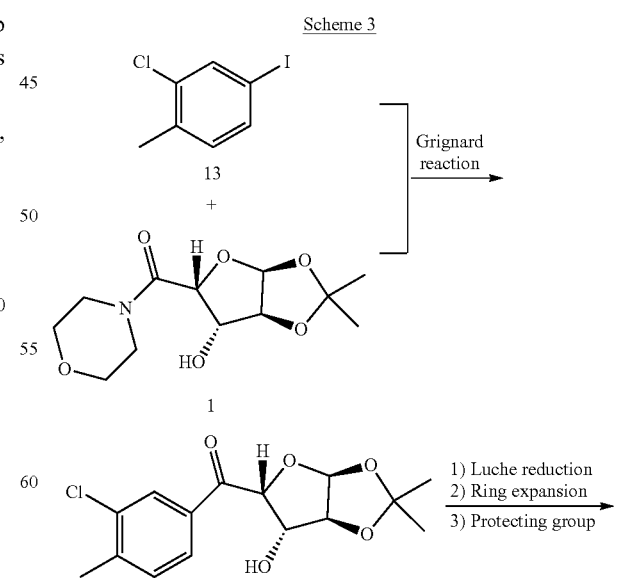

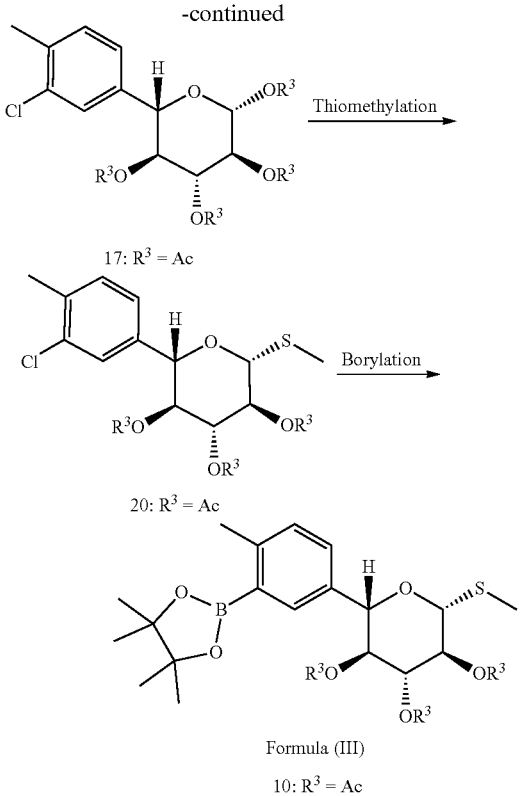

17: R³ = Ac

20: R³ = Ac

Formula (III)

10: R³ = Ac

Compound 13 is treated with a Grignard reagent to prepare the aryl Grignard reagent which is then added to compound 1 pre-treated with a second Grignard reagent to give ketone 14, as described in Example 6.1. Stereoselecive reduction of 14 followed by deprotection, ring expansion and protection gives tetraacetate 17. The thiomethylation is performed by introduction of thiourea to form an adduct which is then converted to a free thiol and treated in situ with methyl iodide, as described in Example 6.3.

Provided herein is a process for preparation of compound 10 by borylation of compound 20, comprising contacting compound 20 with a diboronyl compound, a palladium precatalyst, and a ligand selected from the group consisting of SPhos (2-dicyclohexyl-phosphino-2',6'-dimethoxybiphenyl) and XPhos (2-dicyclohexylphosphino-2',4',6'-triisopropylbiphenyl). In some embodiments, the palladium precatalyst is Pd(OAc)$_2$, the diboronyl compound is bis(pinacolato)diboron (B$_2$pin$_2$), and the ligand is SPhos. In some of such embodiments, the reaction temperature is from about 60° C. to about 80° C. In one example, borylation of the aryl chloride is performed as described in Example 6.4, to obtain a compound of formula (III). In one instance, compound 10 is isolated with a non-aqueous work up.

5.4. Methods of Treatment

Provided herein is a method of treating, preventing or managing a metabolic disease or disorder, which comprises administering to a patient in need of such treatment, prevention or management a therapeutically or prophylactically effective amount of crystalline N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide L-proline. In some embodiments, the metabolic disease or disorder is diabetes. In certain instances, the diabetes is type 1 diabetes. In other instances, the diabetes is type 2 diabetes.

Also contemplated within the scope of embodiments presented herein are methods of treating or managing cardiovascular diseases and disorders, metabolic diseases and disorders, bowel diseases and disorders, and certain types of cancer.

One embodiment of the disclosure encompasses methods of treating a cardiovascular or metabolic disease or disorder, which comprises administering to a patient in need thereof a safe and efficacious amount of an SGLT1 inhibitor of the disclosure (i.e., a compound disclosed herein). Particular cardiovascular diseases and disorders include atherosclerosis, congestive heart failure, diabetes (Type 1 and 2), disorders associated with hemoconcentration (e.g., hemochromatosis, polycythemia vera), hyperglycemia, hypertension, hypomagnesemia, hyponatremia, lipid disorders, obesity, renal failure (e.g., stage 1, 2, or 3 renal failure), and Syndrome X. Particular patients suffer from, or are at risk of suffering from, type 2 diabetes mellitus.

Another embodiment of the disclosure encompasses methods of treating or managing constipation-predominant irritable bowel syndrome (IBS-C) or chronic constipation, which comprise administering to a patient in need thereof a safe and efficacious amount of an SGLT1 inhibitor of the disclosure.

Another embodiment of the disclosure encompasses methods of treating or managing cancer in a patient, which comprise administering to a patient in need thereof a safe and efficacious amount of an SGLT1 inhibitor of the disclosure. Particular types of cancer are those in which the cancer cells exhibit enhanced SGLT gene expression. See, e.g., Calvo, M. B., et al., *Int. J. Endocrinology*, vol. 2010, article ID 205357.

In certain embodiments of the disclosure, a compound of the disclosure is administered adjunctively with another drug or pharmacologically active ingredient ("therapeutic agent"). In the treatment of a cardiovascular or metabolic disease or disorder, examples of second therapeutic agents include those known to be useful in its treatment, such as anti-diabetic agents; anti-hyperglycemic agents; hypolipidemic/lipid lowering agents; anti-obesity agents; anti-hypertensive agents and appetite suppressants.

Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, and dipeptidyl peptidase IV (DPP-4) inhibitors.

Examples of meglitinides include nateglinide (Novartis) and KAD1229 (PF/Kissei).

Examples of thiazolidinediones include Mitsubishi's MCC-555 (disclosed in U.S. Pat. No. 5,594,016), Glaxo-Welcome's GL-262570, englitazone (CP-68722, Pfizer), darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Examples of PPAR-alpha agonists, PPAR-gamma agonists and PPAR alpha/gamma dual agonists include muraglitizar, peliglitazar, AR-H039242 (Astra/Zeneca), GW-409544 (Glaxo-Wellcome), GW-501516 (Glaxo-Wellcome), KRP297 (Kyorin Merck) as well as those disclosed by Murakami et al, *Diabetes* 47, 1841-1847 (1998), WO 01/21602 and in U.S. Pat. No. 6,653,314.

Examples of aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Examples of DPP-4 inhibitors include sitagliptin (Januvia®, Merck), vildagliptin (Galvus®, Novartis), saxagliptin (Onglyza®, BMS-477118), linagliptin (BI-1356), dutogliptin (PHX1149T), gemigliptin (LG Life Sciences), alogliptin (SYR-322, Takeda), those disclosed in WO99/38501, WO99/46272, WO99/67279 (PROBIODRUG), WO99/67278 (PROBIODRUG), and WO99/61431 (PROBIODRUG), NVP-DPP728A (1-[[[2-[(5-cyanopyridin-2-yl)amino]ethyl]amino]acetyl]-2-cyano-(S)-pyrro-lidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, *Bioorg. & Med. Chem. Lett.* 8 (1998) 1537-1540), 2-cyanopyrrolidides and 4-cyanopyrrolidides, as disclosed by Ashworth et al, *Bioorg. & Med. Chem. Lett.*, Vol. 6, No. 22, pp 1163-1166 and 2745-2748 (1996), the compounds disclosed in U.S. application Ser. No. 10/899,641, WO 01/868603 and U.S. Pat. No. 6,395,767, employing dosages as set out in the above references.

Examples of anti-hyperglycemic agents include glucagon-like peptide-1 (GLP-1), GLP-1(1-36) amide, GLP-1(7-36) amide, GLP-1(7-37) (as disclosed in U.S. Pat. No. 5,614,492), exenatide (Amylin/Lilly), LY-315902 (Lilly), liraglutide (Novo Nordisk), ZP-10 (Zealand Pharmaceuticals A/S), CJC-1131 (Conjuchem Inc), and the compounds disclosed in WO 03/033671.

Examples of hypolipidemic/lipid lowering agents include MTP inhibitors, HMG CoA reductase inhibitors, squalene synthetase inhibitors, fibric acid derivatives, ACAT inhibitors, lipoxygenase inhibitors, cholesterol absorption inhibitors, $Na^+$/bile acid co-transporter inhibitors, up-regulators of LDL receptor activity, bile acid sequestrants, cholesterol ester transfer protein (e.g., CETP inhibitors, such as CP-529414 (Pfizer) and JTT-705 (Akros Pharma)), and nicotinic acid and derivatives thereof.

Examples of MTP inhibitors include those disclosed in U.S. Pat. Nos. 5,595,872, 5,739,135, 5,712,279, 5,760,246, 5,827,875, 5,885,983 and 5,962,440.

Examples of HMG CoA reductase inhibitors include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Examples of hypolipidemic agents include pravastatin, lovastatin, simvastatin, atorvastatin, fluvastatin, cerivastatin, and rosuvastatin.

Examples of phosphinic acid compounds useful in inhibiting HMG CoA reductase include those disclosed in GB 2205837.

Examples of squalene synthetase inhibitors include α-phosphono-sulfonates disclosed in U.S. Pat. No. 5,712,396, those disclosed by Biller et al., *J. Med. Chem.* 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., et al., *Current Pharmaceutical Design*, 2, 1-40 (1996).

Examples of additional squalene synthetase inhibitors suitable for use herein include the terpenoid pyrophosphates disclosed by P. Ortiz de Montellano et al., *J. Med. Chem.*, 1977, 20, 243-249, the farnesyl diphosphate analog A and presqualene pyrophosphate (PSQ-PP) analogs as disclosed by Corey and Volante, *J. Am. Chem. Soc.* 1976, 98, 1291-1293, phosphinylphosphonates reported by McClard, R. W. et al., *J.A.C.S.*, 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

Examples of fibric acid derivatives which may be employed in combination with the compounds of this disclosure include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex, Policexide), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary ammonium poly(diallyldimethylammonium chloride) and ionenes, such as disclosed in U.S. Pat. No. 4,027,009, and other known serum cholesterol lowering agents.

Examples of ACAT inhibitors that may be employed in combination compounds of this disclosure include those disclosed in *Drugs of the Future* 24, 9-15 (1999), (Avasimibe); Nicolosi et al., *Atherosclerosis* (Shannon, Irel). (1998), 137(1), 77-85; Ghiselli, Giancarlo, *Cardiovasc. Drug Rev.* (1998), 16(1), 16-30; Smith, C., et al., *Bioorg.*

*Med. Chem. Lett.* (1996), 6(1), 47-50; Krause et al., Editor(s): Ruffolo, Robert R., Jr.; Hollinger, Mannfred A., *Inflammation: Mediators Pathways* (1995), 173-98, Publisher: CRC, Boca Raton, Fla.; Sliskovic et al., *Curr. Med. Chem.* (1994), 1(3), 204-25; Stout et al., *Chemtracts: Org. Chem.* (1995), 8(6), 359-62, or TS-962 (Taisho Pharmaceutical Co. Ltd).

Examples of hypolipidemic agents include up-regulators of LD2 receptor activity, such as MD-700 (Taisho Pharmaceutical Co. Ltd) and LY295427 (Eli Lilly).

Examples of cholesterol absorption inhibitors include SCH48461 (Schering-Plough), as well as those disclosed in *Atherosclerosis* 115, 45-63 (1995) and J. Med. Chem. 41, 973 (1998).

Examples of ileal $Na^+$/bile acid co-transporter inhibitors include compounds as disclosed in *Drugs of the Future*, 24, 425-430 (1999).

Examples of lipoxygenase inhibitors include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., *Brit. J. Pharmacology* (1997) 120, 1199-1206, and Cornicelli et al., *Current Pharmaceutical Design*, 1999, 5, 11-20.

Examples of suitable anti-hypertensive agents for use in combination with compounds of this disclosure include beta adrenergic blockers, calcium channel blockers (L-type and T-type; e.g., diltiazem, verapamil, nifedipine, amlodipine and mibefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of anti-obesity agents include beta 3 adrenergic agonists, lipase inhibitors, serotonin (and dopamine) reuptake inhibitors, thyroid receptor beta drugs, $5HT_{2C}$ agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adiponectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

Examples of beta 3 adrenergic agonists include AJ9677 (Takeda/Dainippon), L750355 (Merck), or CP331648 (Pfizer) or other known beta 3 agonists, as disclosed in U.S. Pat. Nos. 5,541,204, 5,770,615, 5,491,134, 5,776,983 and 5,488,064.

Examples of lipase inhibitors include orlistat and ATL-962 (Alizyme).

Examples of serotonin (and dopamine) reuptake inhibitors (or serotonin receptor agonists) include BVT-933 (Biovitrum), sibutramine, topiramate (Johnson & Johnson) and axokine (Regeneron).

Examples of thyroid receptor beta compounds include thyroid receptor ligands, such as those disclosed in WO97/21993 (U. Cal SF), WO99/00353 (KaroBio) and GB98/284425 (KaroBio).

Examples of monoamine reuptake inhibitors include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol.

Examples of anorectic agents include dexamphetamine, phentermine, phenylpropanolamine, and mazindol.

5.5. Pharmaceutical Compositions

This disclosure encompasses pharmaceutical compositions comprising N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide (compound I), and forms of compound I, such as those described above in Section 5.3, optionally in combination with one or more second active ingredients, such as those described above in Section 5.4. In some embodiments, the pharmaceutical composition comprises Form III as described herein. In some embodiments, the pharmaceutical composition comprises Form II as described herein. In some embodiments, the pharmaceutical composition comprises Form I as described herein.

Certain pharmaceutical compositions are single unit dosage forms suitable for oral administration to a patient. Discrete dosage forms suitable for oral administration include tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., Remington's Pharmaceutical Sciences, 18th ed. (Mack Publishing, Easton Pa.: 1990).

Typical oral dosage forms are prepared by combining the active ingredient(s) in an intimate admixture with at least one excipient according to conventional pharmaceutical compounding techniques. Because of their ease of administration, tablets and capsules represent the most advantageous oral dosage unit forms. If desired, tablets can be coated by standard aqueous or nonaqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

6. EXAMPLES

In the synthetic examples provided herein, reagents and materials were used as received unless otherwise noted.

Unless additional GC or GCMS analysis was necessary, reactions were monitored by reverse-phase HPLC (Shimadzu components, UV detection at 220 nm), generally using a C18 or phenyl-hexyl column with water/MeCN or water/MeOH mobile phase and TFA as a modifier. Melting point information was collected using a differential scanning calorimeter (peak temperature). NMR spectra were acquired in deuterated solvents on Bruker AV 400 MHz ($^1$H) or AV 700 MHz ($^1$H) spectrometers. Mass spectrometry data were obtained during LC-MS analysis (reverse phase Agilent LC/Waters ZQ API-MS with ESCI). Compound purity was assessed by reverse phase HPLC and/or $^1$H NMR.

6.1. Preparation of Compound 14

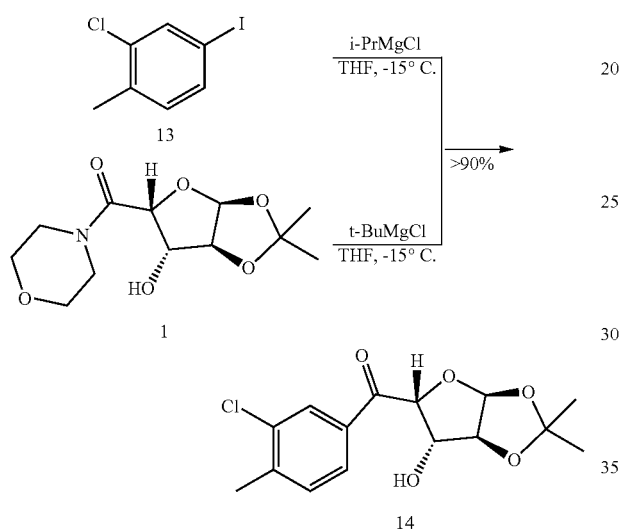

(3-chloro-4-methylphenyl)((3αS,5R,6S,6αS)-6-hydroxy-2,2-dimethyltetrahydrofuro[2,3-d][1,3]dioxol-5-yl)methanone (14). t-Butylmagnesium chloride (~1 M in THF 5.45 L) was added to a solution of morpholinoamide 1 (1.25 kg) in THF (4.5 L) over 1.5 h at −15 to −3° C. and then held at −15° C. In a separate reactor, i-propylmagnesium chloride in THF (2.65 L, 2.11 M) was added to a solution of aryl iodide 13 (1.29 kg) in THF (3.5 L) over 1.5 h at −15° C. and aged until transmetallation was complete. The resulting aryl Grignard solution was then added to the solution of deprotonated morpholinoamide 1 over 10 min at 3° C., aged at −10° C. until reaction completion, and then quenched into a cold (~5° C.) solution of citric acid (1.08 kg) in water (6.75 L). The organic layer was separated, washed twice with 25% brine (2×2.5 L) and concentrated to ~4 L. The resulting suspension was warmed to 50-55° C., n-heptane (6 L) was added and the mixture cooled slowly to 0° C., aged for 1 h, and filtered. The filter-cake was washed with a mixture of n-heptane/THF (4:1, 2.5 L) followed by n-heptane (2 L). The wet-cake was dried under reduced pressure at 40-45° C. with gentle nitrogen sweep to afford 1.30 kg of ketone 14: 91% yield, m.p. 153° C. (DSC peak temperature), LC-MS: calc M+H 313, found, m/z 313; $^1$H NMR (400 MHz, DMSO-$d_6$): δ 1.28 (s, 3H), 1.48 (s, 3H), 2.40 (s, 3H), 4.44 (t, J=3.8 Hz, 1H), 4.48 (d, J=3.8 Hz, 1H), 5.52 (d, J=3.5 Hz, 1H), 5.59 (d, J=5.0 Hz, 1H), 6.02 (d, J=3.5 Hz, 1H), 7.51 (d, J=8.3 Hz, 1H), 7.80 (dd, J=7.9, 1.6 Hz, 1H), 7.89 (d, J=1.8 Hz, 1H); $^{13}$C NMR (101 MHz, DMSO-$d_6$): δ 20.3, 26.7, 27.3, 76.6, 84.8, 85.6, 105.1, 111.7, 127.3, 128.6, 131.9, 134.1, 136.0, 141.4, 193.7

6.2. Preparation of Compound 17

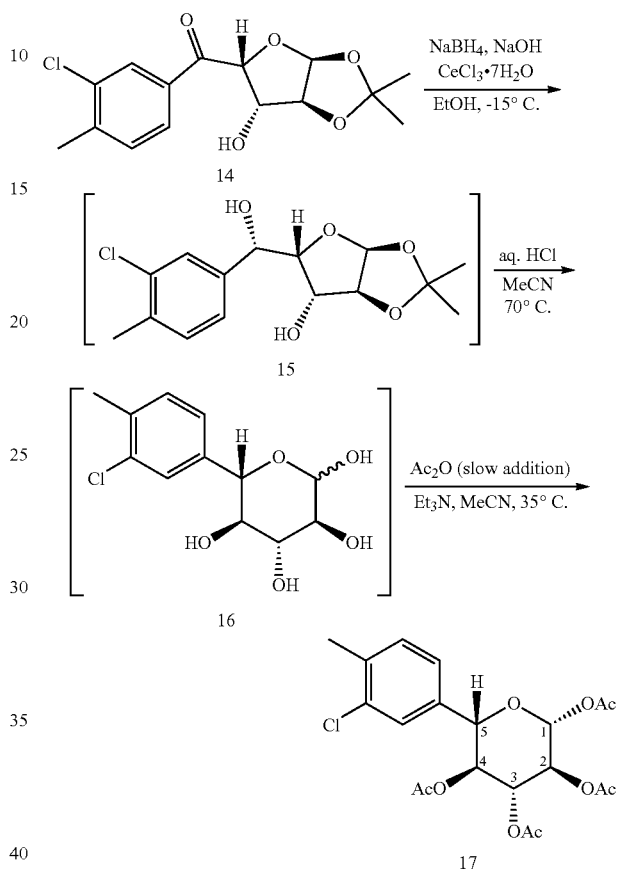

(2R,3S,4R,5S,6S)-6-(3-chloro-4-methylphenyl)tetrahydro-2H-pyran-2,3,4,5-tetrayl tetraacetate (17).

Luche reduction to diol 15. A solution of sodium borohydride (93.95 g) in 1.0 N sodium hydroxide (582 mL) was added to a mixture of ketone 14 (2.00 kg), cerium trichloride heptahydrate (1.19 kg) and ethanol (14 L) over 1.5 h at −19 to −17° C. The reaction mixture was aged until reaction completion (diastereomeric ratio of diol 15=96:4, HPLC). It was warmed to 0° C., quenched with water (8 L) and concentrated to ~11 L. Ethyl acetate (8 L) was added and the pH was adjusted to 2.5 with 6 N HCl (~535 mL). The organic layer was separated, washed sequentially with 0.25 N sodium hydroxide (2×4.5 L) and 25% brine (4 L), distilled to a low volume and then solvent swapped to acetonitrile.

Deprotection to tetraol 16. Water (3.5 L) and 6 N HCl (260 mL) were added to the diol solution 15 and the mixture was aged 65-70° C. for 3.5 h then cooled to 25° C. It was extracted with 2-MeTHF (10 L). The organic phase was washed with 25% brine (2×4 L), concentrated to ~5 L, and then co-distilled with acetonitrile. The precipitate was filtered off to give a solution of tetraol 16 in acetonitrile.

Acetylation to tetraacetate 17. The tetraol 16 solution was diluted with acetonitrile to ~11.5 L and then triethylamine (7.15 L) added followed by slow addition of acetic anhydride (3.62 L) and aging at 34-36° C. until reaction completion. The reaction mixture was cooled to 15° C., quenched with water (18 L) at ≤30° C. The resulting suspension was cooled to 10-15° C., aged and filtered. The collected solid was washed sequentially with 2-propanol (3×4 L) and n-heptane (4 L), and then dried under reduced pressure at 40-45° C. to give 2.11 kg of tetraacetate 17 as an off-white solid: yield 72% (3 steps from 14), m.p. 181° C. (DSC peak temperature), LC-MS: calc M+NH$_4$ 460, found, m/z 460; $^1$H NMR (700 MHz, DMSO-d$_6$): δ 1.80 (s, 3H), 1.96 (s, 3H), 2.04 (s, 3H), 2.08 (s, 3H), 2.32 (s, 3H), 4.92 (d, J=9.7 Hz, 1H), 5.16 (t, J=9.6, 1H), 5.21 (dd, J=9.7, 8.4, 2H), 5.49 (t, J=9.6 Hz, 1H), 6.03 (d, J=8.4 Hz, 1H), 7.23 (dd, J=7.8, 1.3 Hz, 1H), 7.33 (d, J=7.8 Hz, 1H), 7.45 (s, 1H); $^{13}$C NMR (101 MHz, DMSO-d$_6$): δ 19.8, 20.1, 20.3, 20.5, 70.5, 72.3, 72.3, 74.9, 91.6, 126.7, 128.0, 131.5, 133.6, 136.2, 136.4, 169.0, 169.3, 169.6, 170.0.

6.3. Preparation of Compound 20

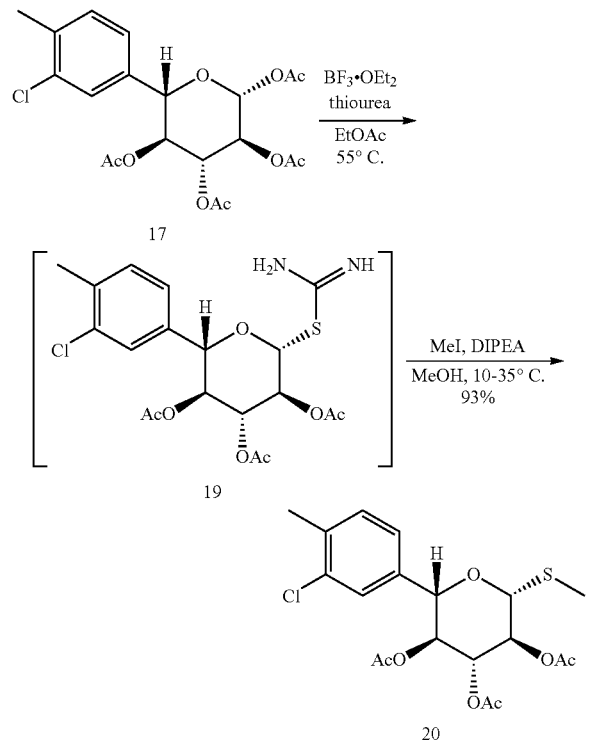

(2S,3S,4R,5S,6R)-2-(3-chloro-4-methylphenyl)-6-(methylthio)tetrahydro-2H-pyran-3,4,5-triyl triacetate (20). Boron trifluoride diethyl etherate (1.46 L) was added to a mixture of tetraacetate 17 (2.09 kg), thiourea (394 g) in ethyl acetate (14 L). The mixture was stirred at 55° C. for 4 h to give the thiourea adduct 19. The reaction mixture was cooled 0° C., methanol (4 L) and methyl iodide (358 mL) were added followed by slow addition of N,N-diisopropylethylamine (3.59 kg). The reaction mixture was stirred at 20-25° C. until reaction completion then concentrated to 8-9 L and flushed with IPA (final volume ~11 L). Water (11 L) was added over 0.5 h and the suspension aged at 35° C. for 0.5 h, 4 h at 10-12° C. The product was filtered, washed sequentially with IPA/water (2:1, 6 L), IPA (3 L), and n-heptane (4 L). Drying under reduced pressure at 40-45° C. gave 1.88 kg of aryl chloride 20 as an off-white solid: 92.7% yield, m.p. 170° C. (DSC peak temperature), LC-MS: calc M+NH$_4$ 448, found, m/z 448; $^1$H NMR (700 MHz, DMSO-d$_6$): δ 1.79 (s, 3H), 1.96 (s, 3H), 2.05 (s, 3H), 2.13 (s, 3H), 2.32 (s, 3H), 4.73 (d, J=9.7 Hz, 1H), 4.89 (d, J=9.9 Hz, 1H), 5.14 (t, J=9.6 Hz, 1H), 5.18 (t, J=9.7 Hz, 1H), 5.37 (t, J=9.4 Hz, 1H), 7.24 (dd, J=7.8, 1.5 Hz, 1H), 7.33 (d, J=8.0 Hz, 1H), 7.46 (s, 1H); $^{13}$C NMR (101 MHz, DMSO-d$_6$) δ 11.0, 19.9, 20.6, 20.8, 20.9, 69.3, 72.6, 73.6, 77.9, 81.8, 126.6, 128.0, 131.5, 133.6, 136.2, 137.0, 169.0, 169.6, 170.0.

6.4. Preparation of Compound 10

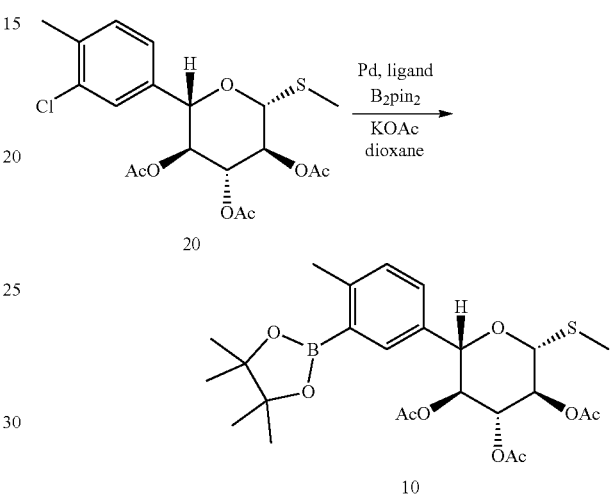

(2S,3S,4R,5S,6R)-2-(4-methyl-3-(4,4,5,5-tetramethyl-1,3,2-dioxaborolan-2-yl)phenyl)-6-(methylthio)tetrahydro-2H-pyran-3,4,5-triyl triacetate (10). A mixture of SPhos (76.2 g), palladium acetate (20.44 g), aryl chloride 20 (2.00 kg), bis(pinacolato)diboron (B$_2$pin$_2$, 1.76 kg), potassium acetate (1.37 kg) and dioxane (16 L) was aged at 60° C. until reaction completion (28 h). The reaction mixture was cooled to 25° C., diluted with isopropyl acetate (IPAc, 10 L), and filtered through a pad of silica gel (4 kg). The filtrate was concentrated to ~2.4 L, diluted to 20 L with IPAc, treated with Darco G-60 (100 g) for 3 h at 50° C. and filtered. This filtrate was concentrated to ~4.5 L, n-heptane (18 L) was added slowly at 50° C., cooled to 5-15° C., and filtered. The filter-cake was washed with n-heptane (2×4 L), and dried under reduced pressure at 45-50° C. to give arylboronic ester 10 as a white solid (2.23 kg, 91% yield). Elemental analysis: calculated C: 57.48%, H: 6.75%, S: 6.14%; found C: 57.42%, H: 6.51%, S: 6.13%; m.p. 149° C. (DSC peak temperature). LC-MS: calc [M+NH$_4$]$_{540}$, found, m/z 540; $^1$H NMR (400 MHz, DMSO-d$_6$): δ 1.27-1.34 (br s, 12H), 1.76 (s, 3H), 1.95 (s, 3H), 2.05 (s, 3H), 2.11 (s, 3H), 2.44 (s, 3H), 4.74 (d, J=9.8 Hz, 1H), 4.92 (d, J=10.0 Hz, 1H), 5.04 (t, J=9.7 Hz, 1H), 5.11 (t, J=9.7 Hz, 1H), 5.35-5.41 (m, 1H), 7.17 (d, J=8.0 Hz, 1H), 7.37 (d, J=7.5 Hz, 1H), 7.57 (d, J=1.8 Hz, 1H); $^{13}$C NMR (101 MHz, DMSO-d$_6$): δ 11.2, 20.6, 20.8, 20.9, 22.1, 25.1, 25.2, 69.6, 72.6, 73.7, 78.5, 82.0, 83.9, 129.7, 130.3, 133.5, 135.2, 144.9, 169.0, 169.6, 169.9.

Alternate Preparation of Compound 10:

A mixture of palladium(II) acetate (0.14 kg), and S-phos (0.5 kg), aryl chloride 20 (12.8 kg,), bis(pinacolato)diboron (11.4 kg), potassium acetate (8.9 kg) in 2-methyltetrahydrofuran (2-MeTHF, 108 kg) was aged at 65-75° C. until reaction completion. It was cooled to 15-25° C., filtered through a pad of silica gel, recirculated through activated carbon cartridges, and then concentrated to approximately 25 L under reduced pressure below 50° C. n-Heptane (106 kg) was added slowly at 40-50° C., and the mixture aged for 1-2 hours, cooled to 5-15° C., and aged for 6-8 hours before the product was filtered. The filter-cake was washed with n-heptane (26 kg), and then dried at 40-50° C. under reduced pressure to give 13.5 kg compound 10 as a white powder (86% yield).

6.5. Preparation of Compound 8

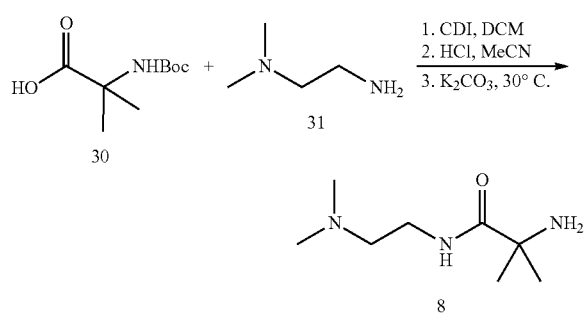

2-Amino-N-(2-(dimethylamino)ethyl)-2-methylpropanamide (8). Boc-α-amino isobutyric acid (Boc-AiB-OH) (30) (3.00 kg) was added in portions over 0.5 h to a suspension of 1,1'-carbonyldiimidazole (CDI, 2.56 kg) in dichloromethane (21 L) at 20-30° C. After stirring for 0.5 h at 20-25° C., N,N-dimethylethylenediamine (1.56 kg) was added at <30° C. over 1 h. The mixture was stirred for 0.5 h, washed with aq. sodium bicarbonate (7.5%, 2×15 L), followed by water (2×15 L). The individual aqueous layers were sequentially extracted with dichloromethane (15 L). The combined organic layer was concentrated to ~6 L, flushed with acetonitrile (12 L in portions), and diluted with acetonitrile (24 L). HCl (4.0 N in dioxane, 9.2 L) was added slowly at <40° C. and the resulting thick suspension stirred at 20-25° C. Potassium carbonate (5.10 kg) was added over 0.5 h (CO$_2$ evolution) and the mixture aged at 30° C. for 16 h. Upon cooling to 20° C., the slurry was filtered, and the filter-cake washed with acetonitrile (9 L). The combined filtrate was concentrated to give product 8 as a brown oil (3.04 kg, 93.6% yield corrected for 78.9 wt % assay). LC-MS: calc [M+H] 174, found, m/z 174; $^1$H NMR (400 MHz, CDCl$_3$): δ 1.36 (s, 6H), 2.25 (s, 6H), 2.42 (t, J=6.3 Hz, 2H), 3.31 (q, J=6.0 Hz, 2H), 7.79 (br. s, 1H); $^{13}$C NMR (101 MHz, CDCl$_3$): δ 29.3, 36.9, 45.4, 54.8, 58.3, 177.6.

Alternative preparation of amine 8.

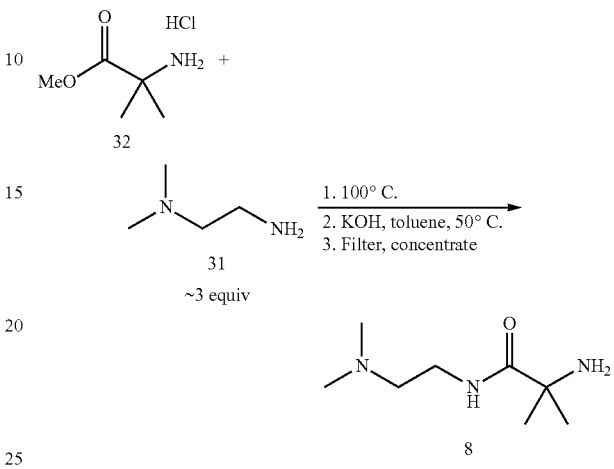

A mixture of N,N-dimethylethylenediamine (4.0 mL) and methyl α-amino isobutyrate hydrochloride (AiB-OMe HCl) (32) (2.00 g,) was aged at 100° C. for 7 h and then cooled to room temperature. Toluene (6 mL) and potassium hydroxide pellets (1.0 g) were added and the mixture was aged at 50° C. for 6 h before cooling to room temperature. The white slurry was filtered through Celite and the filtrate was concentrated under reduced pressure to give amine 8 as a yellow oil (2.25 g, 97% yield); $^1$H NMR (700 MHz, DMSO-d$_6$): δ 1.17 (s, 6H), 1.87 (br. s., 2H), 2.15 (s, 6H), 2.29 (t, J=6.6 Hz, 2H), 3.13 (q, J=6.5 Hz, 2H), 7.88 (br. s., 1H).

6.6. Preparation of Compound 11a

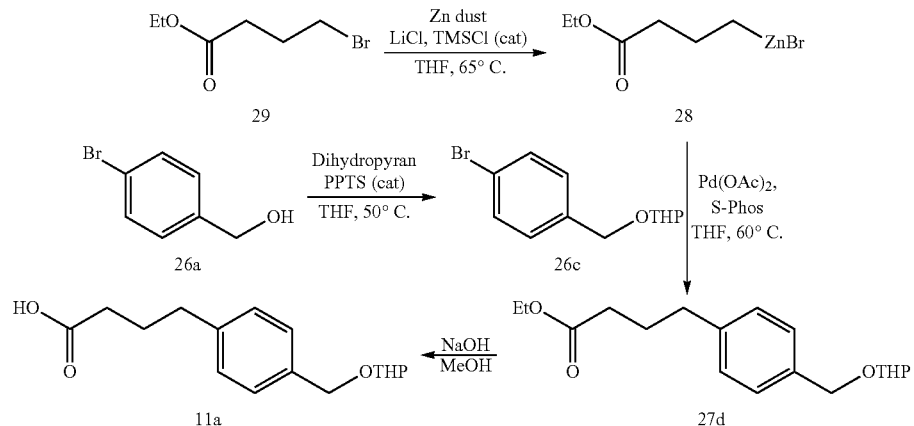

4-(4-(((tetrahydro-2H-pyran-2-yl)oxy)methyl)phenyl)butanoic acid (11a).

Preparation of alkylzinc 28. TMSCl (50.1 g) was added to a mixture of anhydrous LiCl (196 g), zinc dust (726 g), ethyl 4-bromobutanoate (29, 1.80 kg) in THF (2.5 L). The mixture was heated to 55° C. over 0.3 h and aged at 50-65° C. for 2 h, 60-65° C. for 19 h and then cooled to 25° C. Residual zinc particles were settled and the supernatant (~4 L) was used for the Negishi coupling directly.

THP-protected 4-bromobenzyl alcohol 26c. A mixture of 4-bromobenzyl alcohol (26a, 1.16 kg), pyridinium p-toluenesulfonate (32.0 g), and 3,4-dihydropyran (0.571 kg) in THF (3.7 L) was aged at 50° C. until reaction completion, cooled used in the Negishi coupling directly.

Negishi coupling product 27d. To a solution of 26c was added 0.4-0.5 L of the alkylzinc 28 solution and the mixture stirred for 0.5 h at 35-40° C. Meanwhile, a solution of catalyst was prepared by dissolving Pd(OAc)$_2$ (1.39 g) and SPhos (10.2 g) in THF (62 mL) at 20° C. The catalyst solution was charged into the above reaction mixture. After the initial exotherm subsided, the remaining alkylzinc 28 was added at 45-60° C. over 1-2 h. The reaction mixture was aged at 60° C. until reaction completion, cooled to 20° C., quenched with EtOH (359 mL) and aged for 0.5 h. The batch was then concentrated to 3-4 L, diluted with toluene (5 L), water (3.7 L), and 50% aqueous citric acid (150 mL). The organic layer was separated, washed with water (2×2.3 L), concentrated to ~3 L and flushed with toluene (1.3 L×3) to give crude 27d (2.20 kg).

Ester hydrolysis to 11a. Crude ester (27d, 2.20 kg) was diluted with MeOH (1 L) and then 30% NaOH (0.92 L) was added over 0.3 h. After aging for 0.5 h at 30-40° C., toluene (2.30 L) and water (2.30 L) were added, and the resulting mixture was cooled to 20° C. The aqueous layer was separated, mixed with toluene (3.5 L), cooled to 2° C. and slowly acidified to pH 4.1 at <5° C. with 6 N HCl (~1.45 L). The organic layer was separated, washed with water (1.2 L), 1:1 brine/water (1.2 L), concentrated to a low volume and flushed with toluene (~3 L in portions) to give crude product 11a (~3 L) to be used directly in amidation to 9a. $^1$H NMR (700 MHz, CDCl$_3$): δ 1.53-1.69 (m, 4H), 1.72-1.79 (m, 1H), 1.85-1.92 (m, 1H), 1.97 (quin, J=7.5 Hz, 2H), 2.38 (t, J=7.4 Hz, 2H), 2.68 (t, J=7.6 Hz, 2H), 3.56-3.60 (m, 1H), 3.95 (ddd, J=11.4, 8.9, 3.0 Hz, 1H), 4.49 (d, J=12.0 Hz, 1H), 4.73-4.75 (m, 1H), 4.78 (d, J=7.0 Hz, 1H), 7.18 (d, J=8.0 Hz, 2H), 7.31 (d, J=8.0 Hz, 2H); $^{13}$C NMR (101 MHz, CDCl$_3$): δ 19.2, 25.4, 26.2, 30.5, 33.2, 34.6, 62.0, 68.6, 97.6, 128.0, 128.4, 135.8, 140.5, 179.3.

6.7. Preparation of Compound 9b

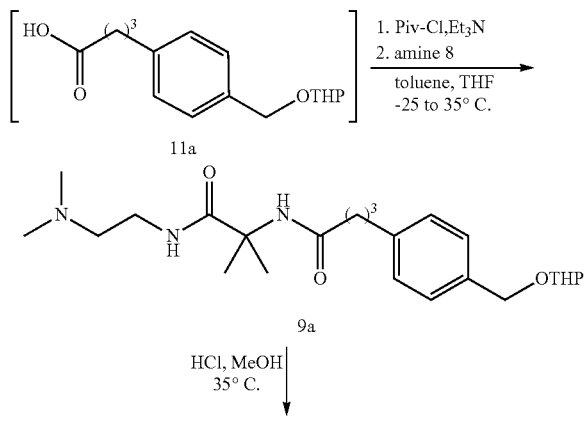

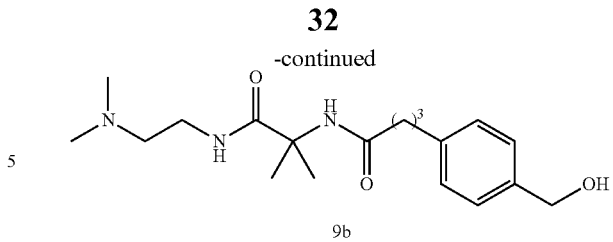

N-(1-((2-(dimethylamino)ethyl)amino)-2-methyl-1-oxopropan-2-yl)-4-(4-(((tetrahydro-2H-pyran-2-yl)oxy)methyl)phenyl)butanamide (9a). A solution of crude 11a (2.64 kg) in toluene (0.6 L), THF (0.6 L), and Et$_3$N (1.05 L) was added slowly (2 h) to a solution of pivaloyl chloride (823 g) in toluene (2.6 L) and THF (0.86 L) at −20 to −30° C. The reaction mixture was aged for 0.3 h at −25° C. and then Et$_3$N (0.822 kg) was added followed by amine 8 (1.48 kg, 87 wt %, 1.28 kg active) at −20 to −25° C. The mixture was aged for 0.5 h at −25° C., then at 35° C. until reaction completion (16 h). It was cooled to 15° C., quenched with water (1.2 L), basified with 30% NaOH (1.26 L) to pH 12.5, and then diluted with water (3.5 L). The organic layer was washed with 1:1 brine/water (3.5 L×2) and the combined aqueous layer was extracted with toluene/THF (1.0:0.3 L). The combined organic phase was concentrated to a low volume, flushed with toluene to give 3.18 kg of crude product 9a. MTBE (6 L) was added, and the mixture aged at 40° C. for 0.5 h and then 30° C. for 1 h. After further dilution with MTBE (0.5 L) and n-heptane (10 L) and aging at 45° C., the suspension was cooled to 15° C., aged and filtered. The filter-cake was washed with 1:1 MTBE/heptane (12 L), and dried at 45° C. under reduced pressure to give 2.41 kg of 9a as a white solid, 89.8% overall yield from 4-bromobenzyl alcohol (26a), m.p. 88° C. (DSC peak temperature). LC-MS: calc [M+H] 434, found, m/z 434; $^1$H NMR (700 MHz, CD$_3$OD): δ 1.42 (s, 6H), 1.51-1.62 (m, 4H), 1.68-1.75 (m, 1H), 1.82-1.92 (m, 3H), 2.21-2.24 (m, 2H), 2.23 (s, 6H), 2.42 (t, J=6.9 Hz, 2H) 2.64 (t, J=7.7 Hz, 2H), 3.28 (t, J=6.9 Hz, 2H), 3.52-3.56 (m, 1H), 3.91 (ddd, J=11.4, 8.6, 3.2 Hz, 1H), 4.45 (d, J=11.6 Hz, 1H), 4.68-4.72 (m, 2H), 7.19 (d, J=8.0 Hz, 2H), 7.27 (d, J=8.0 Hz, 2H); $^{13}$C NMR (176 MHz, CD$_3$OD): δ 20.64, 25.74, 26.75, 28.69, 31.85, 36.18, 36.59, 38.36, 45.65, 57.77, 59.17, 63.46, 70.05, 99.34, 129.33, 129.65, 137.25, 142.6, 175.45, 177.31.

N-(1-((2-(dimethylamino)ethyl)amino)-2-methyl-1-oxopropan-2-yl)-4-(4-(hydroxymethyl)phenyl)butanamide (9b). Concentrated HCl (37%, 544 mL) was slowly added to a solution of 9a (2.36 kg) in MeOH (7.1 L) at <25° C. The mixture was aged at 35° C. until reaction completion (1 h), and then cooled to 0-5° C. Aqueous NaOH (50 wt %, 365 mL) was slowly added until the pH 10-12 at 5-10° C. The reaction mixture was concentrated to ~3 L, flushed with MeOH (1.5 L×4), and then THF (2 L×4) at 45-50° C. The precipitate was filtered off at 40-45° C., and the filter-cake rinsed with THF (~2 L) at 40° C. n-Heptane (9 L) was added to the combined filtrate, and the mixture aged at 30° C. for 0.5 h, 10-15° C. for 3 h. The product was filtered, washed with 2:1 n-heptane/THF (6 L), and dried at 45° C. under reduced pressure to give 1.83 kg of 9b as a white solid: 96.2% yield; m.p. 92° C. (DSC peak temperature); LC-MS: calc [M+H] 350, found, m/z 350; $^1$H NMR (700 MHz, DMSO-d$_6$): δ 1.30 (s, 6H), 1.76 (quin, J=7.6 Hz, 2H), 2.08 (s, 6H), 2.09 (t, J=7.3 Hz, 2H), 2.21 (t, J=6.9 Hz, 2H), 2.54 (t, J=7.6 Hz, 2H), 3.07 (t, J=6.9 Hz, 2H), 4.45 (s, 2H), 7.13 (d, J=8.0 Hz, 2H), 7.22 (d, J=8.0 Hz, 2H); $^{13}$C NMR (176

MHz, DMSO-$d_6$): δ 25.21, 27.03, 34.40, 34.93, 36.82, 45.12, 55.62, 57.88, 62.66, 126.49, 127.98, 139.86, 140.16, 171.44, 173.88.

6.8. Preparation of Compound 9c

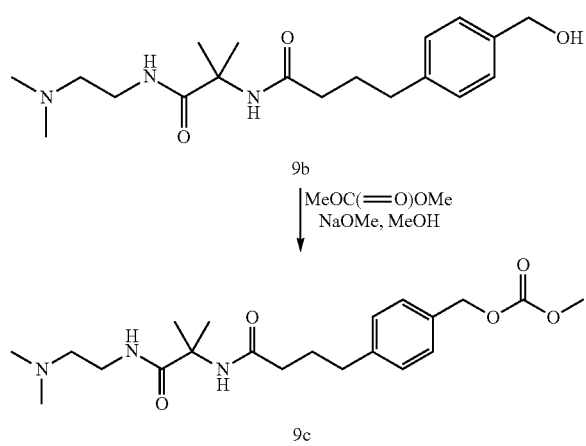

4-(4-((2-(dimethylamino)ethyl)amino)-2-methyl-1-oxo-propan-2-yl)amino)-4-oxobutyl)benzyl methyl carbonate (~4 L). The distillation and dilution operations were repeated until a satisfactory conversion was achieved. The reaction was quenched with $Et_3N \cdot HCl$ (96 g), aged at ambient temperature, and then concentrated to ~5 L. THF (5 L) was added and the resulting thin slurry was filtered. The filtrate was concentrated to ~6 L, then MTBE (8 L) and seed crystals (~10 g) were added at 40° C. n-Heptane (12 L) was then slowly added, and the mixture cooled to 10° C. The product was filtered, washed with 2:1 heptane/MTBE (12 L), and dried under reduced pressure at 40° C. to give 2.82 kg of benzyl carbonate 9c as a white solid: 96.5% yield; m.p. 92° C. (DSC peak temperature); LC-MS: calc [M+H] 408, found, m/z 408; $^1$H NMR (400 MHz, $CDCl_3$): δ 1.55 (s, 6H) 1.94 (quin, J=7.5 Hz, 2H) 2.15-2.24 (m, 8H) 2.43 (t, J=6.0 Hz, 2H) 2.64 (t, J=7.5 Hz, 2H) 3.24-3.36 (m, 2H) 3.78 (s, 3H) 5.12 (s, 2H) 6.28 (s, 1H) 6.79 (br. s., 1H) 7.18 (d, J=7.6 Hz, 2H) 7.26-7.33 (m, 2H); $^{13}$C NMR (101 MHz, $CDCl_3$): δ 25.12, 26.95, 34.78, 36.28, 36.98, 45.05, 54.77, 56.94, 57.60, 69.48, 128.52, 128.68, 132.82, 142.01, 155.67, 172.18, 174.61.

6.9. Preparation of Compound 35

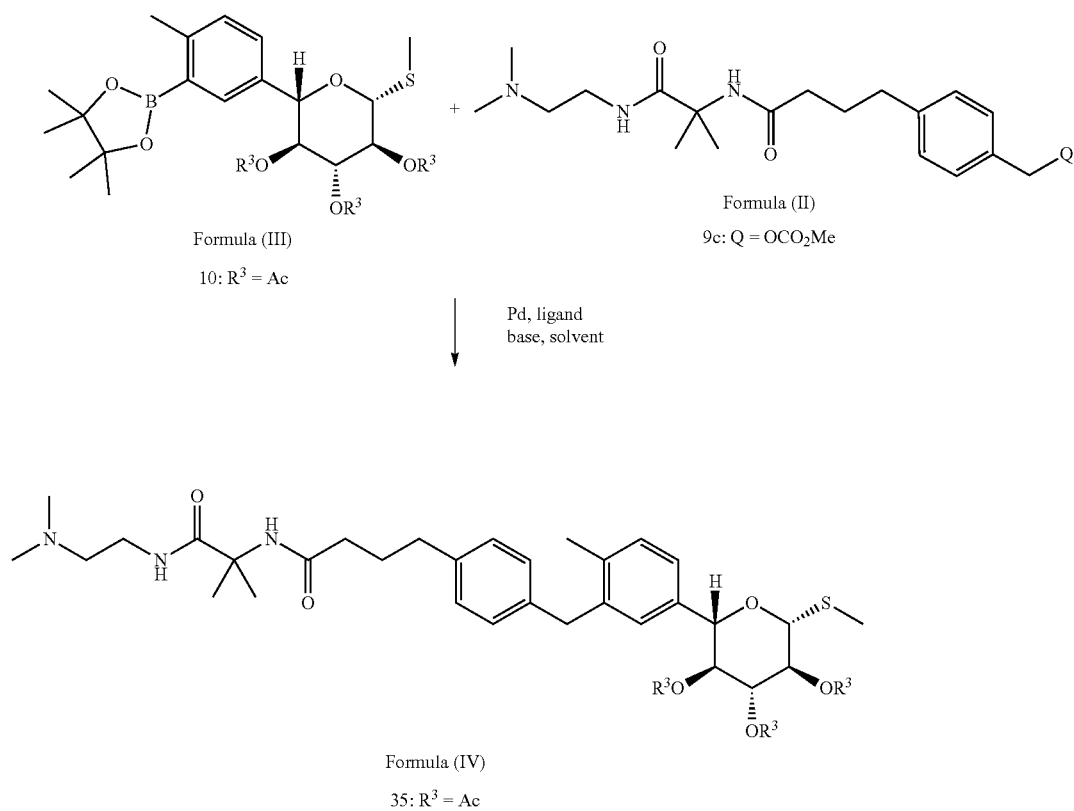

(9c). NaOMe (25 wt % in MeOH) was added to a suspension of 9b (2.50 kg) in dimethyl carbonate (5.0 L) and THF (2 L) and the mixture slowly distilled under reduced pressure. THF (2 L) and dimethyl carbonate (2 L) were added, and the distillation was continued followed by dilution with DMC (2S,3S,4R,5S,6R)-2-(3-(4-(4-((1-((2-(dimethylamino) ethyl)amino)-2-methyl-1-oxopropan-2-yl)amino)-4-oxobutyl)benzyl)-4-methylphenyl)-6-(methylthio)tetra-hydro-2H-pyran-3,4,5-triyl triacetate (35). With stirring, water (22.4 mL) was slowly added to a mixture of arylboronate 10 (651 g), benzyl carbonate 9c (560 g), and potassium carbonate (518 g) in isopropyl alcohol (IPA, 6.5 L). The catalyst solution, prepared separately as described below, was then added, and the reaction mixture was aged at 50° C. until reaction completion (10-20 h).

Preparation of the catalyst solution: A mixture of [Pd(allyl)Cl]$_2$ (2.28 g) and 1,4-diphenylphosphinobutane (DPPbut, 5.84 g) in toluene (130 mL) and IPA (65 mL) was stirred at 20-25° C. for 10-20 min to give the catalyst solution.

Improved catalyst preparation: [Pd(allyl)Cl]$_2$ and DPPbut were combined in toluene at 20-25° C. and stirred for 0.5 h to give a suspension. Immediately before transferring to the reaction mixture, IPA was added to give a yellow-orange solution of the catalyst solution.

After the Suzuki coupling reaction was complete, acetone (7.8-8.0 L) and Darco G-60 (32.5 g) were added and the mixture was stirred at 40° C. for 2-4 h, filtered. The filtrate was concentrated under reduced pressure to 9-10 L at 40° C. Seed of 35 (3.03 g) was added and the mixture stirred for 0.5-1 h, concentrated to ~-10 L, flushed with IPA (3 L), aged at 40° C. for 2 h, rt for 2 h and then filtered. The filter-cake was washed with IPA (2.0 L+1.0 L), n-heptane (1.0 L) and dried under reduced pressure at 40-45° C. to afford 819 g of triacetate 35, as a white solid, 84.5% yield, m.p. 143° C. (DSC peak temperature); LC-MS: calc M+H 728, found m/z 728; $^1$H NMR (400 MHz, DMSO-d$_6$): δ 1.29 (s, 6H), 1.70 (s, 3H), 1.68-1.77 (m, 2H), 1.94 (s, 3H), 2.01-2.14 (m, 14H), 2.15-2.25 (m, 5H), 3.02-3.11 (m, 2H), 3.83-3.98 (m, 2H), 4.66 (d, J=9.8 Hz, 1H), 4.89 (d, J=10.0 Hz, 1H), 5.02-5.17 (m, 2H), 5.30-5.42 (m, 1H), 6.97-7.05 (m, 2H), 7.05-7.25 (m, 6H), 7.83 (s, 1H); $^{13}$C NMR (101 MHz, DMSO-d$_6$): δ 10.8, 19.5, 20.6, 20.8, 20.9, 25.7, 27.5, 34.8, 35.5, 37.4, 38.6, 45.6, 56.2, 58.3, 69.4, 72.8, 73.6, 78.7, 81.5, 125.4, 128.8, 128.9, 129.3, 130.6, 134.8, 136.9, 137.9, 139.4, 139.9, 168.9, 169.6, 169.9, 172.0, 174.4.

Alternate preparation of 35: A mixture of boronate 10 (12.9 kg), benzyl carbonate 9c (11.4 kg), potassium carbonate (0.73 kg), bis(diphenylphosphino)ferrocene (DPPF, 0.67 kg), palladium(II) acetate (0.23 kg), and 2-propanol (113 kg) was aged at 60° C. until reaction completion (12-16 h). The reaction mixture was diluted with acetone (104 kg), cooled to 40-45° C., and filtered. The filtrate was recirculated through activated carbon cartridges, concentrated to ~140 L under reduced pressure below 50° C., flushed with IPA (48 kg+72 kg) below 50° C. with a final volume of ~210 L. The resulting suspension was stirred at 40-45° C. for 4 h, 15-25° C. for 3 h and filtered. The filter-cake was washed with IPA (53 kg) followed by n-heptane (46 kg) and then drying under reduced pressure at 20-45° C. to afford 15.2 kg of 35 as a white solid (82% yield).

6.10. Preparation of Free Base of Compound I

NaOMe (0.5 M in MeOH, 8.9 mL) was added to a mixture of triacetate 35 (6.5 g) in MeOH (89 mL) and the mixture stirred at 20-25° C. for 2 h to complete the deprotection. The reaction was quenched with acetic acid (1.53 mL) and the reaction mixture concentrated under reduced pressure, dissolved in water (32 mL), purified by preparative HPLC and lyophilized to give the formate salt of compound I. The latter was treated with 1 N NaOH, extracted with dichloromethane and concentrated to dryness. The distillation residue (2.0 g) was then dissolved in MeOH (4 mL) and MTBE (11 mL) at 50° C. More MTBE (25 mL) was slowly added and the mixture was stirred for 2 days at 50° C., cooled to 20-25° C. and filtered. The filter-cake was washed with MTBE (8 mL) and dried under reduced pressure at 50° C. give 1.9 g of the free base of compound formula I.

6.11. Preparation of Form I and Form II of Compound I L-Proline Cocrystal

A mixture of N-(1-((2-(dimethylamino)ethyl)-amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide free base (50 mg) and L-proline (9.5 mg) in ethanol (0.5 mL) was stirred at room temperature for 16 h to give a thick suspension. The suspension was filtered and the wet-cake was dried. The wet cake was identified as Form I (an ethanol solvate), which converted to Form II upon drying at 50° C. (DSC peak 147° C.). The solid was used as seeds to prepare 0.7 g more Form II polymorph of the L-proline cocrystal in a similar fashion.

6.12. Preparation of Form III of Compound I L-Proline Cocrystal

A mixture of triacetate 35 (1.207 kg active) in EtOH (6.04 L) was treated with a solution of sodium methoxide in MeOH (25w %, 19.4 mL) at 45° C. for 3-5 h. Then ~50% of a solution of L-proline (220 g) in water (102 mL) and EtOH (485 mL) was added followed by Form III seeds of Compound I L-proline cocrystal (11.9 g) a 40° C. The mixture was stirred at 40° C. for 1 h and the remaining L-proline solution (355 mL) was added slowly over 1 h. The mixture was aged at 40° C. for 1 h, 30° C. for 16 h and then MTBE (10 L) was added slowly. The mixture was aged at 30° C. for 1 h, 20° C. for 2-5 h and then filtered. Thee filter-cake was washed with 2:1 MTBE/EtOH (3.6 L), MTBE (7 L) and dried under reduced pressure at 30-60° C. to give 1.1 kg of form III of compound I L-proline cocrystal, 91.0% yield, m.p. 150° C. (DSC peak temperature); crystalline (XRPD). LC-MS: calc [M+H] 602, found m/z 602; Compound I:L-proline molar ratio, 1.0:1.0 (NMR); $^1$H NMR (700 MHz, CD$_3$OD): δ 1.41 (s, 6H), 1.83-1.90 (m, 2H), 1.92-2.01 (m, 2H), 2.07-2.13 (m, 1H), 2.14 (s, 3H), 2.18-2.22 (m, 5H), 2.25 (s, 6H), 2.26-2.33 (m, 1H), 2.44 (t, J=6.9 Hz, 2H), 2.59 (t, J=7.6 Hz, 2H), 3.18-3.23 (m, 1H), 3.29 (t, J=6.9 Hz, 2H), 3.35-3.42 (m, 3H), 3.45-3.48 (m, 1H), 3.92-3.99 (m, 3H), 4.13 (d, J=9.4 Hz, 1H), 4.39 (d, J=9.5 Hz, 1H), 7.04-7.07 (m, 2H), 7.07-7.11 (m, 2H), 7.12-7.15 (m, 1H), 7.16-7.18 (m, 2H); $^{13}$C NMR (101 MHz, CD$_3$OD): δ 12.0, 19.7, 25.3, 25.7, 28.7, 30.6, 36.1, 36.6, 38.2, 40.2, 45.6, 47.2, 57.7, 59.2, 62.8, 73.9, 76.2, 79.6, 83.7, 87.5, 127.0, 129.6, 129.9, 130.8, 131.2, 137.7, 138.0, 139.5, 140.4, 140.7, 174.4, 175.5, 177.3.

All references cited above are incorporated herein by reference in their entireties.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:
1. A crystalline form of N-(1-((2-(dimethylamino)ethyl)-amino)-2-methyl-1-oxopropan-2-yl)-4-(4-(2-methyl-5-((2S, 3R,4R,5S,6R)-3,4,5-trihydroxy-6-(methylthio)tetrahydro-2H-pyran-2-yl)benzyl)phenyl)butanamide L-proline:

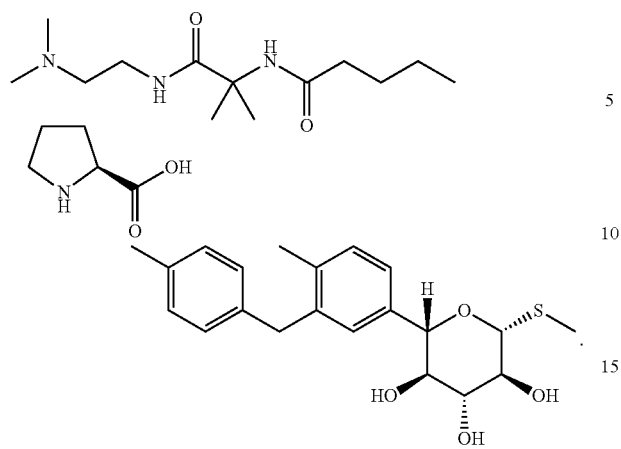

2. The crystalline form of claim 1 having a melting point of 147±5.0° C.

3. The crystalline form of claim 2 having an X-ray powder diffraction pattern comprising peaks at one or more of 4.5, 5.3, 10.5, 12.1, 17.1, 18.8, 19.3, 22.3, 26.1, and 26.2±0.5 degrees 2θ.

4. The crystalline form of claim 1 having a melting point of 150±5.0° C.

5. The crystalline form of claim 4 having an X-ray powder diffraction pattern comprising peaks at one or more of 4.2, 7.5, 8.3, 10.9, 12.5, 14.7, 16.6, 17.7, 19.8, and 20.6±0.5 degrees 2θ.

\* \* \* \* \*